US011903664B2

United States Patent
DiMaio et al.

(10) Patent No.: US 11,903,664 B2
(45) Date of Patent: Feb. 20, 2024

(54) COMPUTER-ASSISTED MEDICAL SYSTEMS AND METHODS

(71) Applicant: Intuitive Surgical Operations, Inc., Sunnyvale, CA (US)

(72) Inventors: Simon Peter DiMaio, San Carlos, CA (US); David William Bailey, Portola Valley, CA (US); Theodore W. Rogers, Alameda, CA (US); Alec Paul Robertson, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 362 days.

(21) Appl. No.: 17/169,188

(22) Filed: Feb. 5, 2021

(65) Prior Publication Data

US 2021/0153961 A1 May 27, 2021

Related U.S. Application Data

(63) Continuation of application No. 16/311,333, filed as application No. PCT/US2017/039917 on Jun. 29, 2017, now Pat. No. 10,939,973.

(Continued)

(51) Int. Cl.
*A61B 34/35* (2016.01)
*A61B 34/37* (2016.01)
(Continued)

(52) U.S. Cl.
CPC .............. *A61B 34/35* (2016.02); *A61B 17/34* (2013.01); *A61B 34/30* (2016.02); *A61B 34/37* (2016.02);
(Continued)

(58) Field of Classification Search
CPC ......... A61B 34/35; A61B 34/37; A61B 17/34; A61B 34/30; A61B 34/70; A61B 2034/305; A61B 2034/302
See application file for complete search history.

(56) References Cited

U.S. PATENT DOCUMENTS

| 5,397,323 | A | 3/1995 | Taylor et al. |
| 5,855,583 | A | 1/1999 | Wang et al. |

(Continued)

FOREIGN PATENT DOCUMENTS

| CN | 105338920 | 2/2016 |
| JP | 2002530209 A | 9/2002 |

(Continued)

OTHER PUBLICATIONS

Baerlocher, P. et al., "Task Priority Formulations for the Kinematic Control of Highly Redundant Articulated Structures," IEEE/RSJ International Conference on Intelligent Robots and Systems, 1998, vol. 1, pp. 323-329.

(Continued)

*Primary Examiner* — Julian W Woo
(74) *Attorney, Agent, or Firm* — Osha Bergman Watanabe & Burton LLP

(57) ABSTRACT

A computer-assisted medical system includes a manipulator arm and an instrument holder physically coupled to the manipulator arm. The instrument holder is configured to releasably couple to an instrument. The instrument holder includes an adjustable assembly and a cannula clamp physically coupled to the adjustable assembly. A physical adjustment of the adjustable assembly moves the cannula clamp relative to the manipulator arm. The cannula clamp is configured to releasably couple to a cannula configured to receive the instrument.

24 Claims, 15 Drawing Sheets

Related U.S. Application Data

(60) Provisional application No. 62/357,678, filed on Jul. 1, 2016.

(51) Int. Cl.
  *A61B 17/34* (2006.01)
  *A61B 34/30* (2016.01)
  *A61B 34/00* (2016.01)

(52) U.S. Cl.
  CPC ........ *A61B 34/70* (2016.02); *A61B 2034/302* (2016.02); *A61B 2034/305* (2016.02)

(56) References Cited

U.S. PATENT DOCUMENTS

| | | | |
|---|---|---|---|
| 6,343,243 | B1 | 1/2002 | Brogaardh et al. |
| 6,424,885 | B1 | 7/2002 | Niemeyer et al. |
| 6,451,027 | B1 | 9/2002 | Cooper et al. |
| 6,786,896 | B1 | 9/2004 | Madhani et al. |
| 7,789,875 | B2 | 9/2010 | Brock et al. |
| 7,974,681 | B2 | 7/2011 | Wallace et al. |
| 8,004,229 | B2 | 8/2011 | Nowlin et al. |
| 8,151,661 | B2 | 4/2012 | Schena et al. |
| 8,541,970 | B2 | 9/2013 | Nowlin et al. |
| 8,624,537 | B2 | 1/2014 | Nowlin et al. |
| 8,749,189 | B2 | 6/2014 | Nowlin et al. |
| 8,749,190 | B2 | 6/2014 | Nowlin et al. |
| 8,786,241 | B2 | 7/2014 | Nowlin et al. |
| 8,816,628 | B2 | 8/2014 | Nowlin et al. |
| 8,823,308 | B2 | 9/2014 | Nowlin et al. |
| 9,532,849 | B2 * | 1/2017 | Anderson .............. A61B 90/57 |
| 10,939,973 | B2 | 3/2021 | DiMaio et al. |
| 2003/0018412 | A1 | 1/2003 | Kimura et al. |
| 2003/0109780 | A1 | 6/2003 | Coste-Maniere et al. |
| 2004/0024385 | A1 | 2/2004 | Stuart et al. |
| 2006/0161136 | A1 | 7/2006 | Anderson et al. |
| 2010/0204713 | A1 | 8/2010 | Ruiz Morales |
| 2011/0060346 | A1 | 3/2011 | Jensen et al. |
| 2011/0213383 | A1 | 9/2011 | Lee et al. |
| 2013/0090552 | A1 | 4/2013 | Ramamurthy et al. |
| 2013/0211590 | A1 | 8/2013 | Diolaiti et al. |
| 2014/0222207 | A1 | 8/2014 | Bowling et al. |
| 2015/0032126 | A1 | 1/2015 | Nowlin et al. |
| 2015/0051733 | A1 | 2/2015 | Nowlin et al. |
| 2016/0157941 | A1 | 6/2016 | Anvari et al. |
| 2016/0235490 | A1 | 8/2016 | Srivastava et al. |
| 2017/0020615 | A1 | 1/2017 | Koenig et al. |
| 2017/0371321 | A1 | 12/2017 | Motoyoshi et al. |
| 2018/0049737 | A1 | 2/2018 | Swayze et al. |
| 2019/0231458 | A1 | 8/2019 | DiMaio et al. |

FOREIGN PATENT DOCUMENTS

| | | |
|---|---|---|
| WO | WO-9950721 A1 | 10/1999 |
| WO | WO-2006124390 A2 | 11/2006 |
| WO | WO-200775844 A1 | 7/2007 |
| WO | WO-2011143020 A1 | 11/2011 |
| WO | WO-2013181516 A1 | 12/2013 |
| WO | WO-2014028699 A1 | 2/2014 |
| WO | WO-2014028703 A1 | 2/2014 |
| WO | WO-2014146085 A1 | 9/2014 |
| WO | WO-2015142953 A1 | 9/2015 |
| WO | WO-2015175200 A1 | 11/2015 |
| WO | WO-2016043845 A1 | 3/2016 |
| WO | WO-2016064616 A1 | 4/2016 |
| WO | WO-2016090459 A1 | 6/2016 |
| WO | WO-2016144998 A1 | 9/2016 |
| WO | WO-2016183054 A1 | 11/2016 |

OTHER PUBLICATIONS

Funda J., et al., "Constrained Cartesian Motion Control for Teleoperated Surgical Robots," IEEE Transactions on Robotics and Automation, IEEE, Jun. 1996, vol. 12 (3), pp. 453-465.

International Search Report and Written Opinion for Application No. PCT/US2017/051846, dated Jan. 10, 2018, 11 pages (ISRG08990/PCT).

International Search Report issued in corresponding International Application No. PCT/US2017/039917, dated Oct. 16, 2017, 12 pages (ISRG06490/PCT).

Jamshidi et al., "Robotics and Manufacturing—Recent Trends in Research, Education and Applications," Proceedings of the Second International Symposium of Robotics and Manufacturing: Research, Education, and Applications, ASME Press, Nov. 16-18, 1988, 17 pages.

Long J.A., et al., "Development of Miniaturized Light Endoscope-holder Robot for Laparoscopic Surgery," Journal of Endourology, Aug. 2007, vol. 21 (8), pp. 911-914.

Maciejewski A.A., et al., "Obstacle Avoidance for Kinematically Redundant Manipulators in Dynamically Varying Environments," International Journal of Robotics Research, 1985, vol. 4 (3), pp. 109-116.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Written Opinion issued in corresponding International Application No. PCT/US2017/039917, dated Oct. 16, 2017, 12 pages (ISRG06490/PCT).

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Various: "Frequency-division Multiplexing," Internet Citation, May 19, 2009 (May 19, 2009), pp. 1-2, XP002623124, Retrieved from the Internet: URL:https://en.wikipedia.org/w/index.php?title=Frequencydivision%20multiplexing%20&oldid=2 90920661 [retrieved on Feb. 17, 2011].

* cited by examiner

COMPUTER-ASSISTED MEDICAL SYSTEMS AND METHODS

CROSS REFERENCE TO RELATED APPLICATIONS

This application is a continuation of and claims the benefit of priority under 35 U.S.C. § 120 to U.S. patent application Ser. No. 16/311,333, filed on Dec. 19, 2018, which is incorporated by referenced herein in its entirety. U.S. patent application Ser. No. 16/311,333 is a national phase application of International Application No. PCT/US2017/039917, which filed on Jun. 29, 2017. International Application No. PCT/US2017/039917 claims priority to U.S. Provisional Patent Application Ser. No. 62/357,678, which filed on Jul. 1, 2016. The disclosure of U.S. Provisional Patent Application Ser. No. 62/357,678 is considered part of and is incorporated by reference in the disclosure of this application.

TECHNICAL FIELD

This disclosure relates to systems and methods for computer-assisted surgery, such as minimally invasive surgery, tele-operated surgery, and minimally invasive computer-assisted tele-operated surgery. For example, the disclosure relates to mechanisms for holding a surgical instrument at the end of a robotic manipulator and methods for actuating computer-assisted insertion motions of the surgical instrument.

BACKGROUND

Robotic systems and computer-assisted devices often include robot or movable arms to manipulate instruments for performing a task at a work site and at least one robot or movable arm for supporting an image capturing device which captures images of the work site. A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often avoiding the trauma generally associated with accessing a surgical worksite by open surgery techniques. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

This disclosure provides systems and methods for computer-assisted medical procedures. Example procedures include surgery, such as minimally invasive surgery, tele-operated surgery, and minimally invasive computer-assisted tele-operated surgery using a computer-assisted tele-operated medical device. Other example procedures include various medical treatments and diagnosis procedures. For example, the disclosure provides mechanisms for holding a medical instrument at the end of a robotic manipulator assembly and methods for actuating axial translations or insertion motions of the instrument.

In the context of minimally invasive computer-assisted medical procedures, movement of the robotic manipulator assembly may be controlled by a processor of the system so that a shaft or intermediate portion of the surgical instrument is constrained to a safe motion through a minimally invasive surgical access site, natural orifice including oral and anal orifices, or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the robotic manipulator assembly motion at the access site may be imposed using in part or in full using robotic data processing and control techniques. Such concepts for constraining the robotic manipulator assembly motion may be referred to herein as software-constrained remote center of motion.

In one aspect, the disclosure is directed to a minimally invasive computer-assisted surgery method that includes moving a computer-assisted surgery manipulator arm to cause an elongate surgical instrument coupled to the computer-assisted surgery manipulator arm to move along a fixed line in space that is defined by a longitudinal axis of the surgical instrument, and moving the surgical instrument along the fixed line in space independent of the computer-assisted surgery manipulator arm movement. The computer-assisted surgery manipulator arm may be tele-operated.

Such a minimally invasive computer-assisted surgery method may optionally include one or more of the following features. At least a distal end portion of the surgical instrument may be disposed inside a patient's body during each of the moving operations. The moving operations may occur at least somewhat contemporaneously. The moving operations may occur noncontemporaneously. The movement of the surgical instrument independently of computer-assisted surgery manipulator arm movements may include moving an instrument holder carriage to which the surgical instrument is releasably coupled. Moving the computer-assisted surgery manipulator arm may be used for long, slow movements and moving the surgical instrument may be used for shorter, quicker movements. The long, slow movements may be distinguished from the shorter, quicker movements by a frequency cut-off filtering operation. Moving the computer-assisted surgery manipulator arm in combination with the moving the surgical instrument may be performed in response to receiving a surgical instrument commanded motion input. Moving the computer-assisted surgery manipulator arm may further include pivoting a surgical instrument holder in relation to the computer-assisted surgery manipulator arm.

In another aspect, this disclosure is directed to a computer-assisted surgery system including: (a) an instrument holder configured for pivotable attachment to a computer-assisted surgery manipulator arm; (b) an instrument holder carriage movably coupled to the instrument holder; (c) a surgical instrument coupleable to the instrument holder carriage, the surgical instrument comprising an elongate shaft and an end effector disposed at an end of the elongate shaft; and (d) a tubular cannula defining a first lumen for slidably receiving the elongate shaft, wherein the tubular cannula is configured for use detached from the instrument holder.

Such a computer-assisted surgery system may optionally include one or more of the following features. The instrument holder may define a second lumen for slidable engagement with the elongate shaft. The instrument holder carriage may be linearly translatable along the instrument holder. The system may also include the computer-assisted surgery manipulator arm coupled to a base.

In another aspect, a computer-assisted surgery system includes an instrument holder coupleable to a computer-assisted surgery manipulator arm, an instrument holder carriage movably coupled to the instrument holder, and a cannula holder coupled to the instrument holder. While the instrument holder is coupled to the computer-assisted surgery manipulator arm, the instrument holder carriage is moveable independent of the computer-assisted surgery manipulator arm, and the cannula holder is moveable independent of the computer-assisted surgery manipulator arm and independent of the instrument holder carriage.

Such a computer-assisted surgery system may optionally include one or more of the following features. The system may also include a cannula that is releasably coupleable to the cannula holder, wherein the cannula defines a lumen. The system may also include a surgical instrument that is releasably coupleable to the instrument holder carriage (wherein the surgical instrument is slidably coupleable within the lumen of the cannula). The instrument holder carriage may be linearly translatable along the instrument holder. The system may also include the computer-assisted surgery manipulator arm coupled to a base.

In another aspect, the disclosure is directed to a computer-assisted surgery system including: (a) an instrument holder configured for pivotable attachment to a computer-assisted surgery manipulator arm; (b) an instrument holder carriage movably coupled to the instrument holder; (c) a surgical instrument coupleable to the instrument holder carriage (the surgical instrument including an elongate shaft and an end effector disposed at an end of the elongate shaft); (d) a cannula holder movably coupled to the instrument holder; and (e) a tubular cannula coupleable to the cannula holder (the tubular cannula defines a lumen for slidably receiving the elongate shaft).

Such a computer-assisted surgery system may optionally include one or more of the following features. The instrument holder carriage may be linearly translatable along the instrument holder. The system may also include the computer-assisted surgery manipulator arm coupled to a base. The cannula holder may be linearly translatable in relation to the instrument holder.

In another aspect, the disclosure is directed to a computer-assisted surgery system including: (a) an instrument holder configured for attachment to a computer-assisted surgery manipulator arm at a pivotable joint (wherein the pivotable joint is translatable along the instrument holder); (b) an instrument holder carriage movably coupled to the instrument holder; (c) a tubular cannula coupleable to the instrument holder (wherein the tubular cannula defines a lumen); and (d) a surgical instrument coupleable to the instrument holder carriage. The surgical instrument includes an elongate shaft and an end effector disposed at an end of the elongate shaft. The elongate shaft is slidably coupleable within the lumen.

Such a computer-assisted surgery system may optionally include one or more of the following features. The instrument holder carriage may be linearly translatable along the instrument holder. The system may also include the computer-assisted surgery manipulator arm coupled to a base.

Some or all of the embodiments described herein may provide one or more of the following advantages. For example, some robotic manipulator assembly embodiments described herein are configured more compactly in comparison to conventional robotic manipulator assemblies. Such compact designs can reduce the potential for physical interference between robotic manipulator assemblies of a robotic surgery system. In addition, such compact designs can reduce the weight and inertia of robotic manipulator assemblies. Consequently, the size and power of the actuators of the robotic surgery system can be reduced. The structural size and weight of the mechanical linkages may also be reduced using the robotic manipulator assembly embodiments described herein. Such lighter mechanical linkages can facilitate a robotic surgery system that is more responsive to user input. In addition, some methods provided herein also facilitate smaller and more responsive robotic manipulator assemblies.

The details of one or more embodiments are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 2:
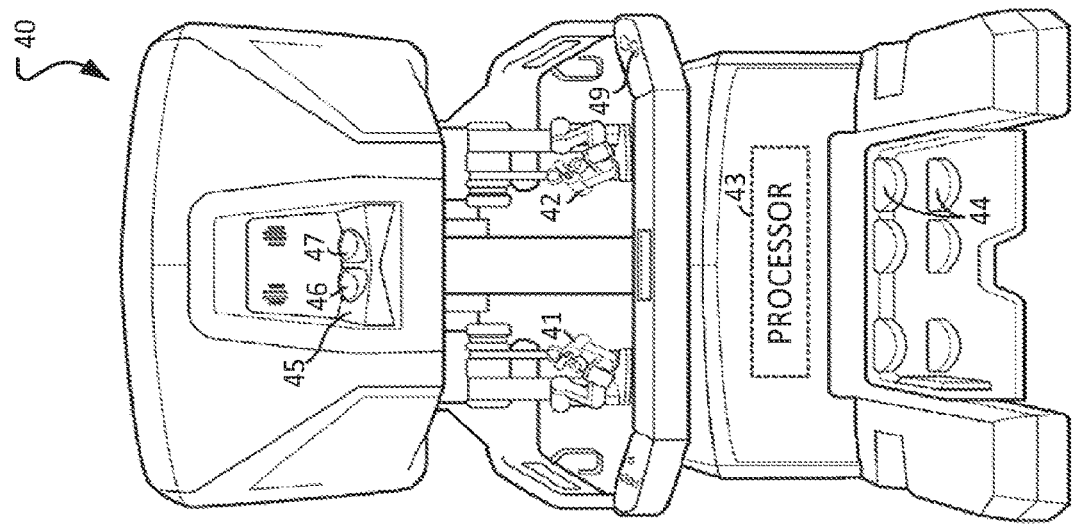
FIG. 2 is a front view of an example surgeon console of a robotic surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention are described primarily in terms of an implementation using a da Vinci® Surgical System, commercialized by Intuitive Surgical, Inc. of Sunnyvale, California Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinc® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in relatively smaller, hand-held, hand-operated devices and in relatively larger systems that have additional mechanical support, as well as in other embodiments of computer-assisted devices, including non-teleoperated and tele-operated medical devices used in medical procedures of all types, such as procedures for diagnosis, non-surgical treatment, minimally invasive surgical treatment, and non-minimally invasive surgical treatment. As applicable, inventive aspects may be embodied and implemented non-medical systems such as industrial robot and other robotic systems.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be dimensionally scaled down to a 5 mm shaft diameter due to mechanical, material property, and manufacturing considerations. Likewise, a 5 mm shaft diameter device cannot simply be dimensionally scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure provides improved medical and robotic devices, systems, and methods. The inventive concepts can be used with computer-assisted medical systems, such as medical robotic systems in which a plurality of surgical tools or instruments will be mounted on and moved by an associated plurality of robotic manipulators during a medical procedure. The robotic systems will often comprise minimally invasive, non-teleoperated, telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive, natural orifice, or other access site. The large number of degrees of freedom may also allow a processor to position the manipulators so as to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery or other medical procedure, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Figure 1:
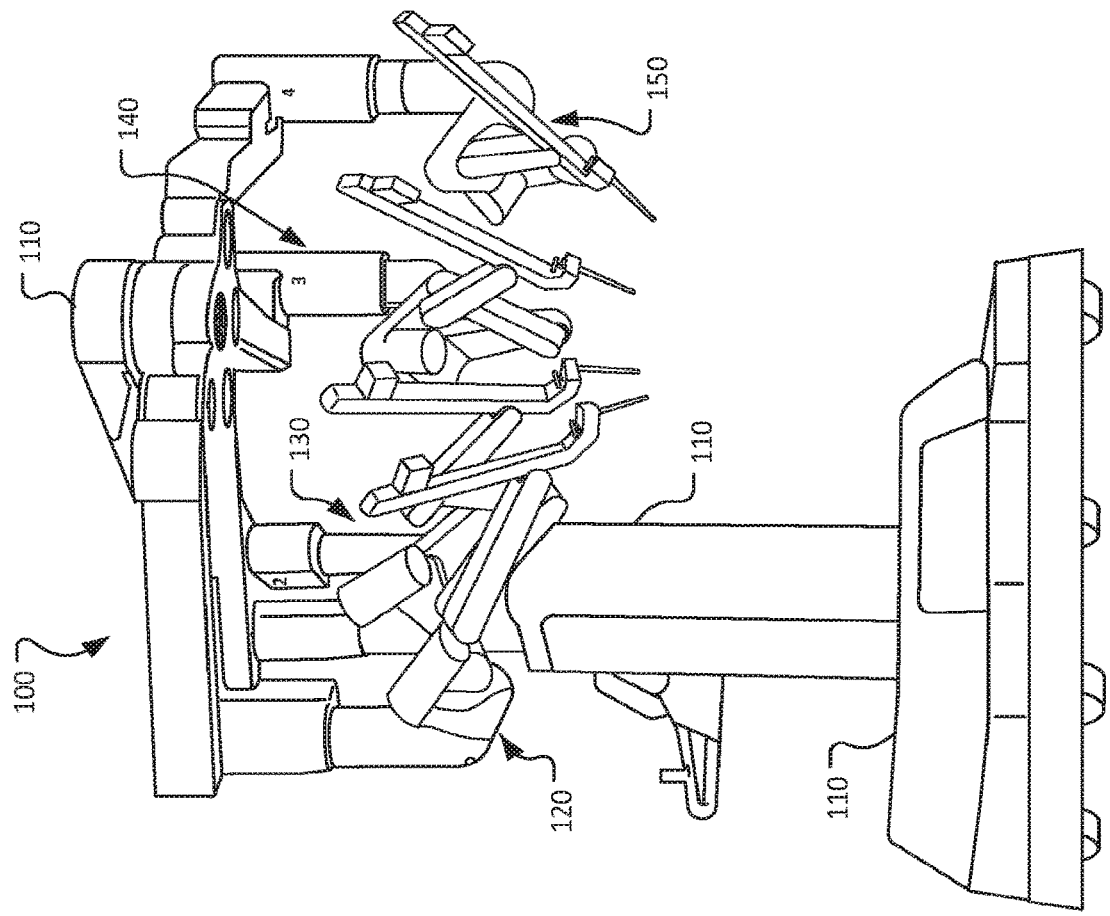
FIG. 1 is a perspective view of an example patient-side cart of a robotic surgery system.

Referring to FIGS. 1 and 2, systems for minimally invasive telesurgery can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. For example, controlling the patient-side cart 100 with the surgeon console 40 is a type of telesurgery. In contrast, directly controlling the patient-side cart by manually pushing or pulling the manipulators or instruments into desired configurations comprise non-teleoperated control. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the telesurgery system.

Figure 3:
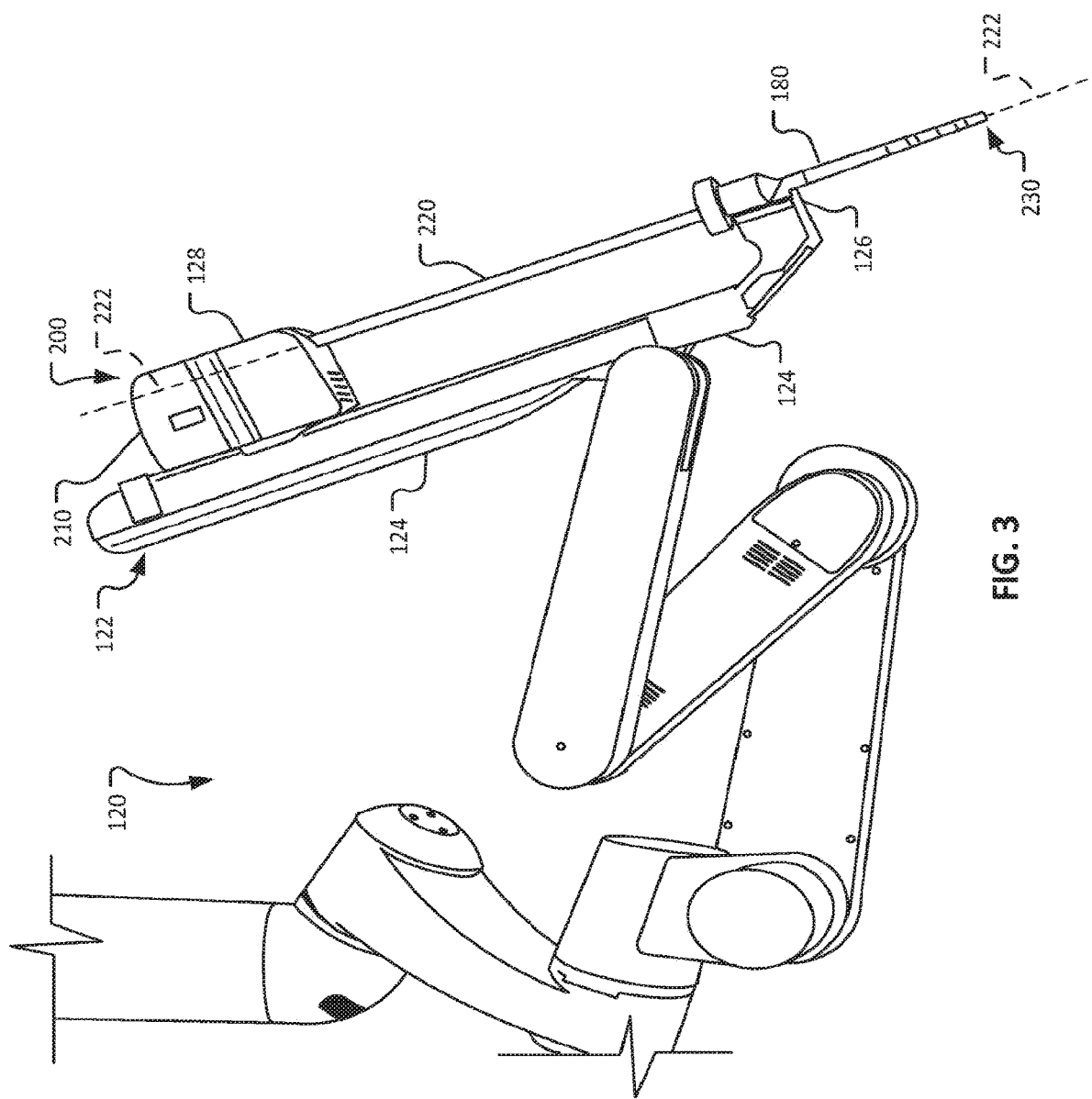
FIG. 3 is a side view of an example robotic manipulator arm assembly of a robotic surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable by the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably coupleable with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
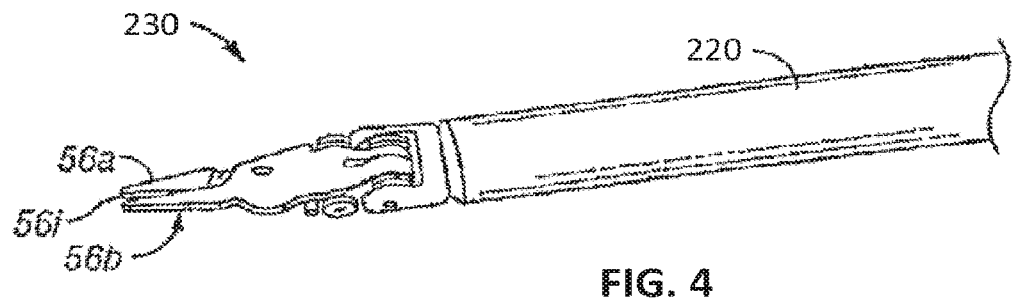
FIG. 4 is a perspective view of a distal end portion of an example surgical instrument in a first configuration.
Figure 5:
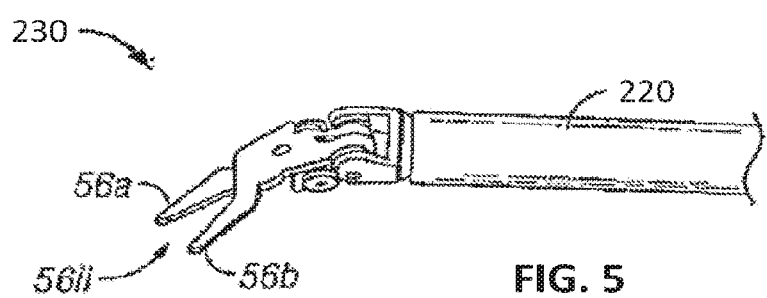
FIG. 5 is a perspective view of the distal end portion of the surgical instrument of FIG. 4 in a second configuration.
Figure 6:
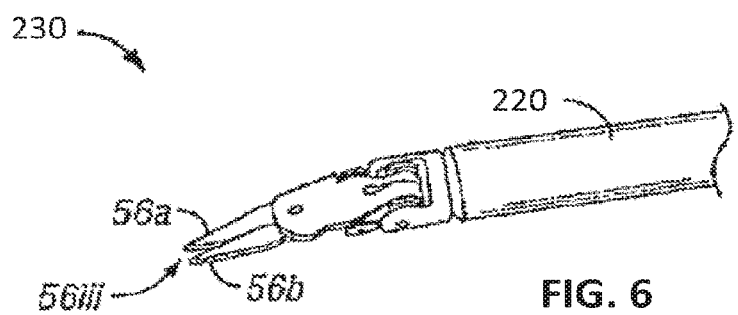
FIG. 6 is a perspective view of the distal end portion of the surgical instrument of FIG. 4 in a third configuration.

Also referring to FIGS. 4-6, a variety of alternative robotic surgical instruments of different types and differing end effectors 230 may be used, with the instruments of at least some of the manipulators being removed and replaced during a surgical procedure. Several of these end effectors, including, for example, DeBakey Forceps 56$i$, microforceps 56$ii$, and Potts scissors 56$iii$ include first and second end effector elements 56$a$, 56$b$ which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

The elongate shaft 220 allow the end effector 230 and the distal end of the shaft 220 to be inserted distally into a surgical worksite through a minimally invasive aperture (via cannula 180), often through an abdominal wall or the like. The surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Referring to FIGS. 7-10, an example robotic manipulator arm assembly 304 can be coupled with a surgical instrument 306 to affect movements of the instrument 306 relative to a base 302. As a number of different surgical instruments having differing end effectors may be sequentially mounted on each robotic manipulator arm assembly 304 during a surgical procedure (typically with the help of a surgical assistant), an instrument holder 320 will preferably allow rapid removal and replacement of the mounted surgical instrument 306. It should be understood that the example robotic manipulator arm assembly 304 is merely one non-limiting example of a variety of types of robotic manipulator arm assemblies envisioned within the scope of this disclosure.

The example robotic manipulator arm assembly 304 is mounted to the base 302 by a pivotal mounting joint 322 so as to allow the remainder of robotic manipulator arm assembly 304 to rotate about a first joint axis J1, with the first joint 322 providing rotation about a vertical axis in the exemplary embodiment. Base 302 and first joint 322 generally comprise a proximal portion of robotic manipulator arm assembly 304, with the manipulator extending distally from the base toward instrument holder 320 and end effector 50.

Figure 7:
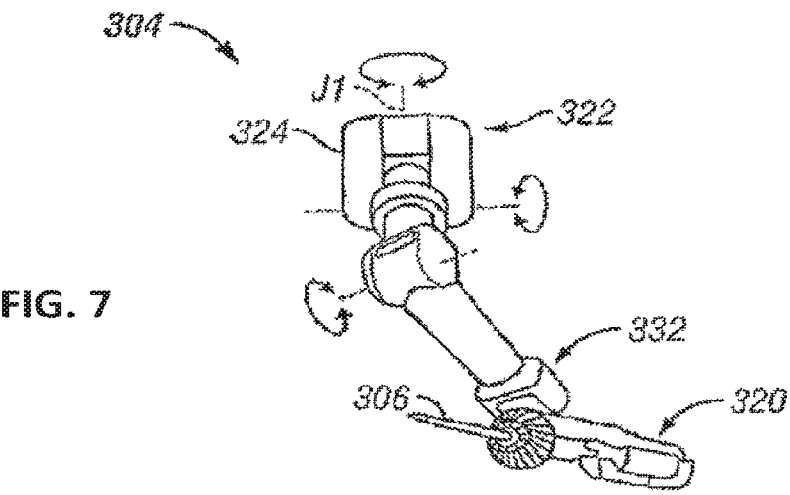
FIGS. 7-9 are bottom, side, and back views of an exemplary robotic manipulator assembly having a range of joint states for a given end effector position.
Figure 8:
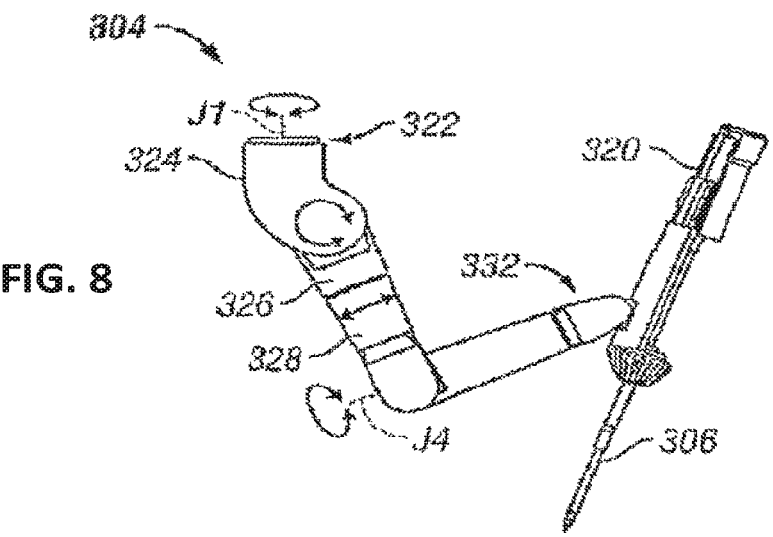
Figure 9:
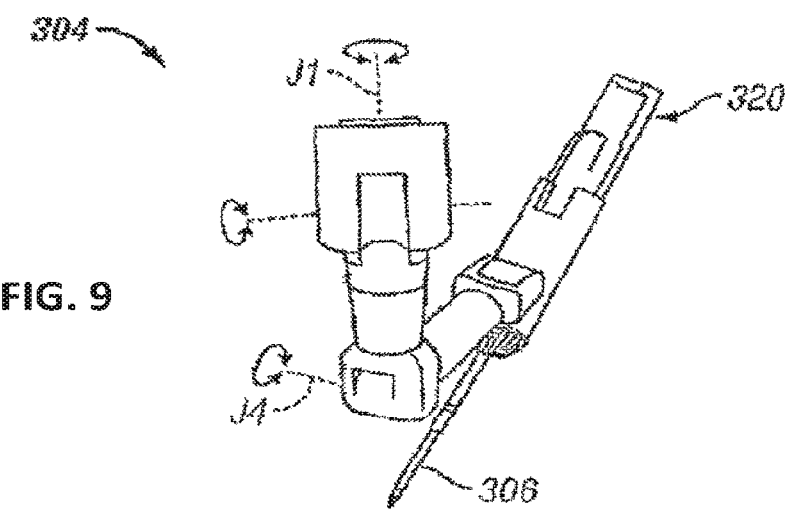
Figure 10:
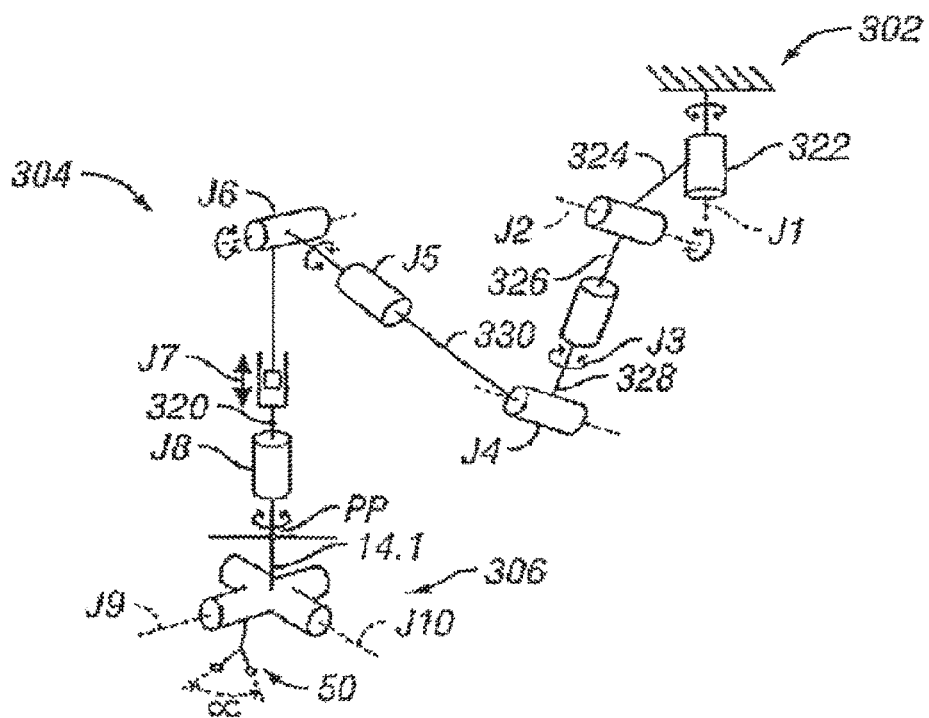
FIG. 10 is a schematic diagram illustrating the degrees of freedom provided by the robotic manipulator assembly of FIGS. 7-9.

Describing the individual links of the robotic manipulator arm assembly 304 as illustrated in FIGS. 7-9, along with the axes of rotation of the joints connecting the links as illustrated in FIG. 10, a first link 324 extends distally from base 302 and rotates about first pivotal joint axis J1 at joint 322. Many of the remainder of the joints can be identified by their associated rotational axes in FIG. 10. For example, a distal end of first link 324 is coupled to a proximal end of a second link 326 at a joint providing a horizontal pivotal axis J2. A proximal end of a third link 328 is coupled to the distal end of the second link 326 at a roll joint so that the third link generally rotates or rolls at joint J3 about an axis extending along (and ideally aligned with) axes of both the second and third links. Proceeding distally, after another pivotal joint J4, the distal end of a fourth link 330 is coupled to instrument holder 320 by a pair of pivotal joints J5, J6 that together define an instrument holder wrist 332. A translational or prismatic joint J7 of the robotic manipulator arm assembly 304 facilitates axial movement of instrument 306 through the minimally invasive aperture, and also facilitates attachment of the instrument holder 320 to a cannula through which the instrument 306 is slidably inserted.

Distally of instrument holder 320, the surgical instrument 306 may include additional degrees of freedom. Actuation of the degrees of freedom of the surgical instrument 306 will often be driven by motors of the robotic manipulator arm assembly 304. Alternative embodiments may separate the surgical instrument 306 from the supporting manipulator arm structure at a quickly detachable instrument holder/instrument interface so that one or more joints shown here as being on the surgical instrument 306 are instead on the interface, or vice versa. In other words, the interface between the surgical instrument 306 and robotic manipulator arm assembly 304 may be disposed more proximally or distally along the kinematic chain of the manipulator arm assembly 304 (which may include both the surgical instrument and the manipulator arm assembly 304). In the exemplary embodiment, the surgical instrument 306 includes a rotational joint J8 proximally of the pivot point PP, which generally is disposed at the site of a minimally invasive aperture. A distal wrist of the surgical instrument 306 allows pivotal motion of end effector 50 about instrument wrist joint axes J9, J10. An angle α between end effector jaw elements may be controlled independently of the end effector 50 location and orientation.

Figure 11:
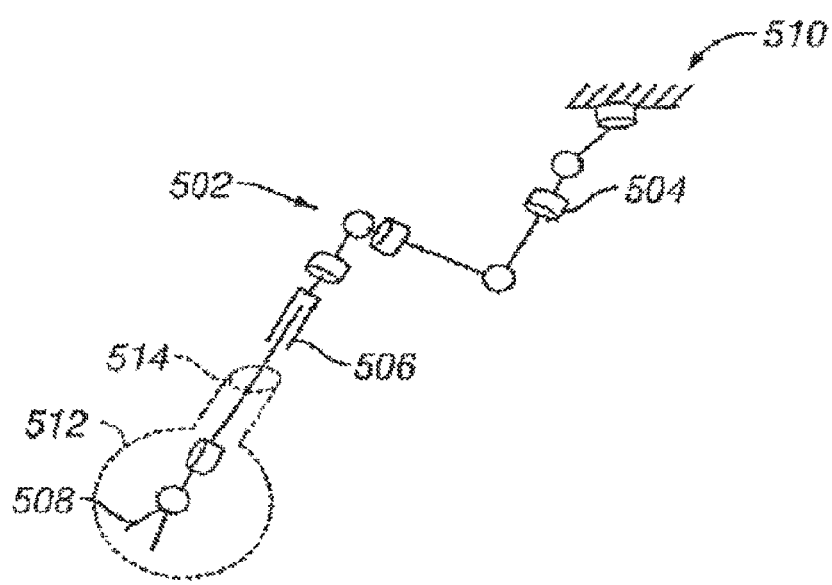
FIG. 11 is a schematic diagram illustrating a robotic manipulator assembly inserted through a surgical aperture.
Figure 12:
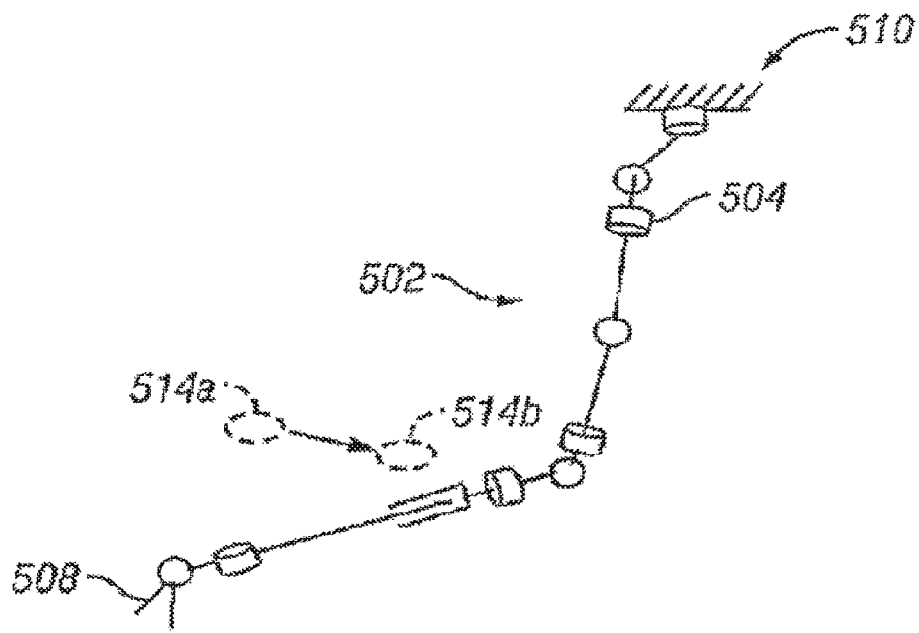
FIG. 12 schematically illustrates some of the challenges in manually repositioning the highly configurable manipulator assembly of FIG. 11 to a new aperture position.
Figure 13:
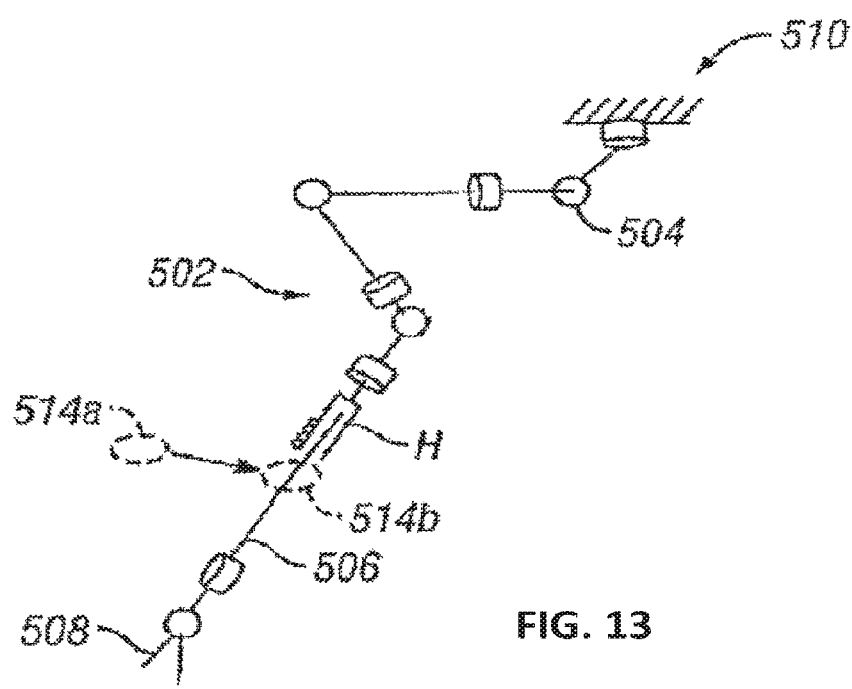
FIG. 13 schematically illustrates reconfiguring of the arm of FIG. 11 so as to enhance range of motion or the like during manual repositioning of the manipulator to a new aperture position.

Referring now to FIGS. 11-13, an example robotic manipulator arm assembly 502 includes a manipulator arm assembly 504 and a surgical instrument 506 having an end effector 508. The term manipulator assembly, as used herein, may in some cases also encompass the manipulator arm without the surgical instrument mounted thereon. The illustrated robotic manipulator arm assembly 502 generally extends from a proximal base 510 distally to the end effector 508, with the end effector 508 and distal portion of the surgical instrument 506 configured for insertion into an internal surgical site 512 via a minimally invasive surgical access 514. The joint structure of the robotic manipulator arm assembly 502 is similar to that described above regarding FIG. 10, and includes sufficient degrees of freedom to allow the manipulator assembly to be anywhere within a range of differing joint states for a given end effector position, even when the surgical instrument 506 is constrained to passage through minimally invasive aperture 514.

When the access site to a minimally invasive surgical procedure is to be changed from a first aperture location 514a to a second aperture location 514b, it will often be desirable to manually reposition some or all of the links of the robotic manipulator arm assembly 502. Similarly, when initially setting up the robotic manipulator assembly 502 for surgery, the manipulator assembly 502 may be manually moved into a desired position aligned with the aperture location through which the associated surgical instrument 506 is to access the surgical site 512. However, in light of the highly configurable manipulator arm structure having a relatively large number of joints between (for example) base 510 and the instrument/manipulator interface (see FIG. 10), such manual positioning of the links can be challenging. Even when the robotic manipulator assembly 502 structure is balanced to avoid gravitational effects, attempting to align each of the joints in an appropriate arrangement can be difficult for one person, time consuming, and may involve significant training and/or skill. The challenges can be even greater when the links of the robotic manipulator assembly 502 are not balanced about the joints, as positioning such a highly configurable structures in an appropriate configuration to begin surgery can be a struggle due to the manipulator's arm length and its passive and limp design.

To facilitate setting up the robotic manipulator assembly 502 for a surgical procedure (or to facilitate reconfiguring the manipulator assembly 502 for accessing a different tissue of the patient), the processor 43 of surgeon console 40 (see FIG. 2) may actively drive joints of the manipulator assembly during 502. In some cases, such driving may be in response to manual movement of at least one joint of the manipulator assembly 502. In FIG. 13, a hand H of a system operator (optionally a surgeon, assistant, technician, or the like) manually moves a link of the robotic manipulator arm assembly 502 or the surgical instrument 506 into alignment with a desired minimally invasive aperture 514b. During this movement, the processor drives joints proximal of the hand/manipulator engagement. As the robotic manipulator arm assembly 502 will often have sufficient degrees of freedom so as to be in a range of alternative configurations, the proximal joints may be driven to a desired manipulator state without inhibiting the manual positioning of the distal portion of the robotic manipulator arm assembly 502. Optionally, the joints may be driven so as to compensate for gravity, to inhibit momentum effects, to provide a desired (and often readily overcome) resistance to the manual movement so as to give the hand the impression of plastically deforming the manipulator structure at its joints, so as to keep the configurable linkage assembly in a desired pose, or the like. While this movement is shown in FIG. 13 as being performed with the surgical instrument 506 attached to the robotic manipulator arm assembly 504, the manipulator assembly will often be manually positioned prior to attachment of the surgical instrument 506 to the robotic manipulator arm assembly 504.

Figure 14:
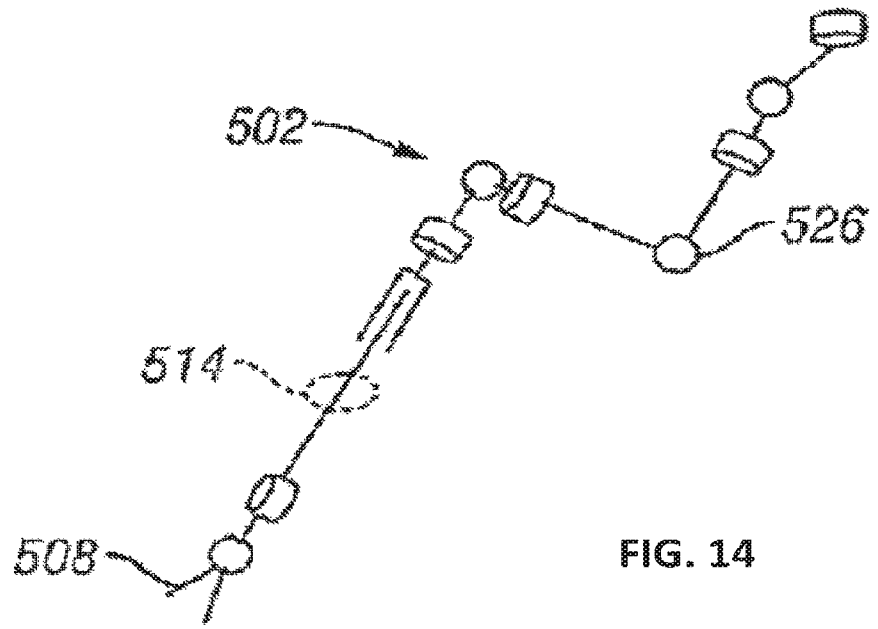
FIGS. 14 and 15 schematically illustrate robotically reconfiguring of the joints of the manipulator assembly within a range of alternative joint configurations during manual movement of the arm.
Figure 15:
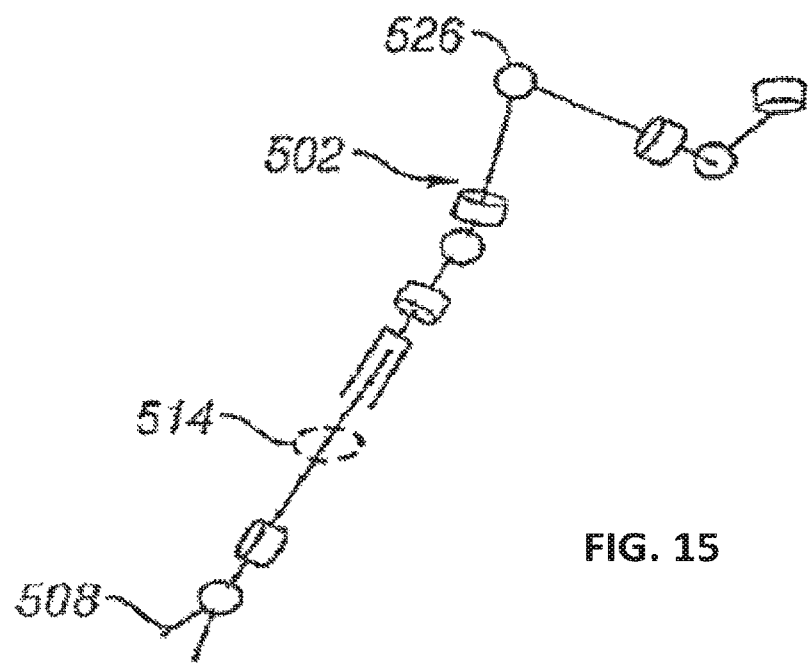

Referring to FIGS. 14 and 15, the robotic manipulator assembly 502 may be reconfigured by the processor 43 (FIG. 2) for any of a variety of differing reasons. For example, a joint 526 may be driven from a downward oriented apex configuration to an upward oriented apex configuration so as to inhibit collisions with an adjacent arm, equipment, or personnel; to enhance a range of motion of the end effector 508; in response to physiological movement of the patient such as patient breathing or the like; in response to repositioning of the patient, such as by reorienting a surgical table; and the like. Some, but not all, of these changes in configuration of the robotic manipulator assembly 502 may be in response to external forces applied to the manipulator assembly 502, with the processor 43 often driving a different joint of the manipulator assembly 502 than that which is being acted upon by the external force. In other cases, the processor 43 will reconfigure the robotic manipulator assembly 502 in response to calculations performed by the processor 43. In either case, the processor 43 may vary from a simple master-slave controller to drive the robotic manipulator assembly 502 in response to a signal to provide a preferred manipulator assembly 502 configuration. Such configuring of the robotic manipulator assembly 502 may occur during master-slave end effector movements, during manual or other reconfiguration of the manipulator assembly 502, and/or at least in part at a different time, such as after releasing a clutch input.

Figure 16:
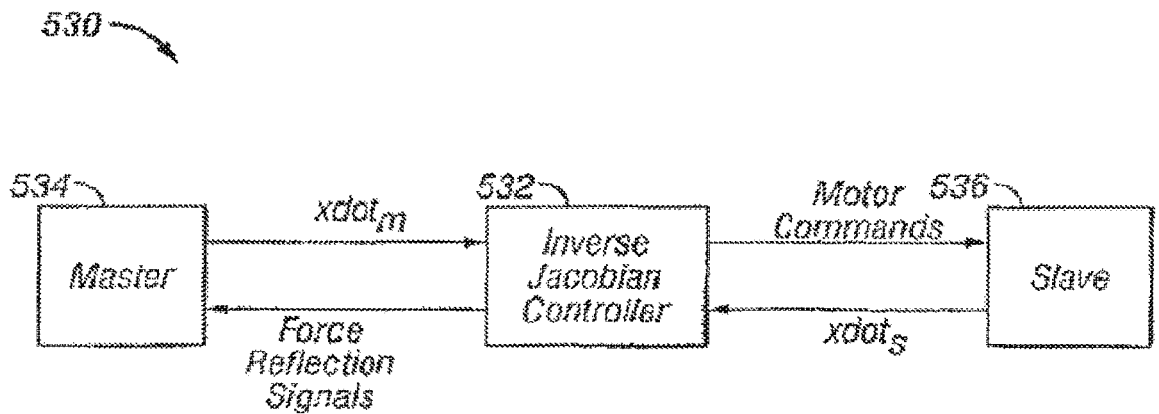
FIG. 16 is a simplified block diagram schematically illustrating a fully constrained inverse Jacobian master/slave velocity controller.

Referring now to FIG. 16, a simplified controller schematic diagram 530 shows a master/slave controller 532 coupling a master input device 534 to a slave manipulator 536. In this example, the controller inputs, outputs, and computations are described using vector mathematical notation in which the vector x will often refer to a position vector in a Cartesian coordinates, and in which the vector q will reference a joint articulation configuration vector of an associated linkage (most often of the manipulator slave linkage), sometimes referred to as the linkage position in joint space. Subscripts can be appended to these vectors to identify a specific structure when ambiguity might otherwise exist, so that $x_m$ (for example) is a position of the master input device in the associated master workspace or coordinate system, while $x_s$, indicates a position of the slave in the workspace. Velocity vectors associated with the position vectors are indicated by a dot over the vector or the word "dot" between the vector and the subscript, such as $xdot_m$ or $\dot{x}_m$ for the master velocity vector, with the velocity vectors being mathematically defined as the change in the position vector with a change in time ($dx_m/dt$ for the master velocity vector example).

Example controller 532 comprises an inverse Jacobian velocity controller. Where $x_m$ is a position of the master input device and $\dot{x}_m$ is the velocity of the master input device, the controller 532 calculates motor commands for transmission to the manipulator 536 to effect slave end effector motions that correspond to the input device from the master velocities. Similarly, controller 532 can calculate force reflection signals to be applied to the master input device (and from there to the operator's hand) from the slave position $x_s$ and/or slave velocity $\dot{x}_s$. A number of refinements to this simple master/slave inverse Jacobian controller schematic are desirable, including those illustrated in FIG. 19 and described in detail in U.S. Pat. No. 6,424,885 ("the '885 patent"), the full disclosure of which is incorporated herein by reference.

Figure 17:
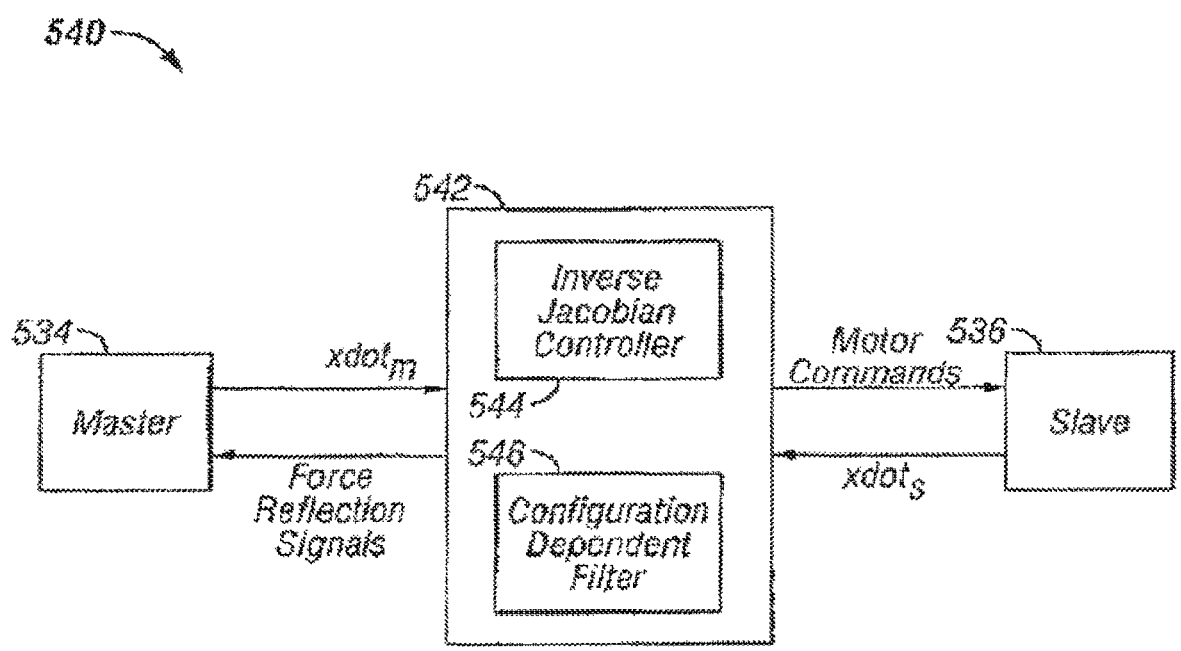
FIG. 17 is a simplified diagram of a modified master/slave controller in which an inverse Jacobian controller module is combined with a second module having a configuration dependent subspace filter to allow control over a manipulator assembly.

Referring now to FIG. 17, a processor 542 (also called "controller 542") may be characterized as including a first controller module 544 and a second controller module 546. The first module 544 may comprise a primary joint controller, such as an inverse Jacobian master-slave controller. The primary joint controller of first module 544 may be configured for generating the desired manipulator assembly movements in response to inputs from the master input device 534. However, as noted above, many of the manipulator linkages described herein have a range of alternative configurations for a given end effector position in space. As a result, a command for the end effector to assume a given position could result in a wide variety of different joint movements and configurations, some of which may be much more desirable than others. Hence, the second module 546 may be configured to help drive the manipulator assembly to a desired configuration, in some embodiments driving the manipulator toward a preferred configuration during master-slave movements. In many embodiments, second module 546 will comprise a configuration dependent filter.

In broad mathematical terms, both the primary joint controller of first module 544 and the configuration dependent filter of second module 546 may comprise filters used by processor 542 to route control authority for linear combinations of joints to the service of one or more surgical goals or tasks. If we assume that X is the space of joint motion, F(X) might be a filter giving control over the joints to i) provide a desired end effector movement, and ii) provide pivotal motion of the instrument shaft at the aperture site. Hence, the primary joint controller of first module 544 may comprise filter F(X). Conceptually, $(1-F^{-1}F)(X)$ could describe a configuration dependent subspace filter giving control actuation authority to the linear combination of joint velocities that are orthogonal to serving the goal of the primary joint controller (in this example, end effector movement and pivotal instrument shaft motion). Hence, this configuration dependent filter could be used by the second module 546 of controller 542 to service a second goal, such as maintaining a desired pose of the manipulator assembly, inhibiting collisions, or the like. Both filters may be further sub-divided into more filters corresponding to serving more specific tasks. For example, filter F(X) could be separated into $F_1(X)$ and $F_2(X)$ for control of the end effector and control of the pivotal shaft motion, respectively, either of which may be chosen as the primary or highest priority task of the processor.

While the mathematical calculations performed by the modules may (at least in part) be similar, the robotic processors and control techniques described herein will often make use of a primary joint controller configured for a first (sometimes referred to as a primary) controller task, and a configuration dependent filter which makes use of an under-constrained solution generated by the primary joint controller for a second (also referred to as secondary) task. In much of the following description, the primary joint controller will be described with reference to a first module, while the configuration dependent filter will be described with reference to a second module. Additional functions (such as additional subspace filters) and or additional modules of varying priorities may also be included.

As noted elsewhere herein, the hardware and/or programming code for performing the functions described with reference to such first and second modules may be fully integrated, partially integrated, or fully separate. Controller 542 may employ the functions of the two modules simultaneously, and/or may have a plurality of differing modes in which one or both modules are used separately or in different ways. For example, in some embodiments, first module 544 might be used with little or no influence from second module 546 during master-slave manipulations, and the second module 546 having a greater role during setup of the system when the end effector is not being driven robotically, such as during port clutching or other manual articulations of the manipulator assembly. Nonetheless, in many embodiments both modules may be active most of or all the time robotic motion is enabled. For example, by setting gains of the first module to zero, by setting $x_s$ to $x_{s,\ actual}$, and/or by reducing the matrix rank in the inverse Jacobian controller so that it doesn't control as much and letting the configuration dependent filter have more control authority, the influence of the first module on the state of the manipulator assembly can be reduced or eliminated so as to change a mode of processor 542 from a tissue manipulator mode to a clutch mode.

Figure 18:
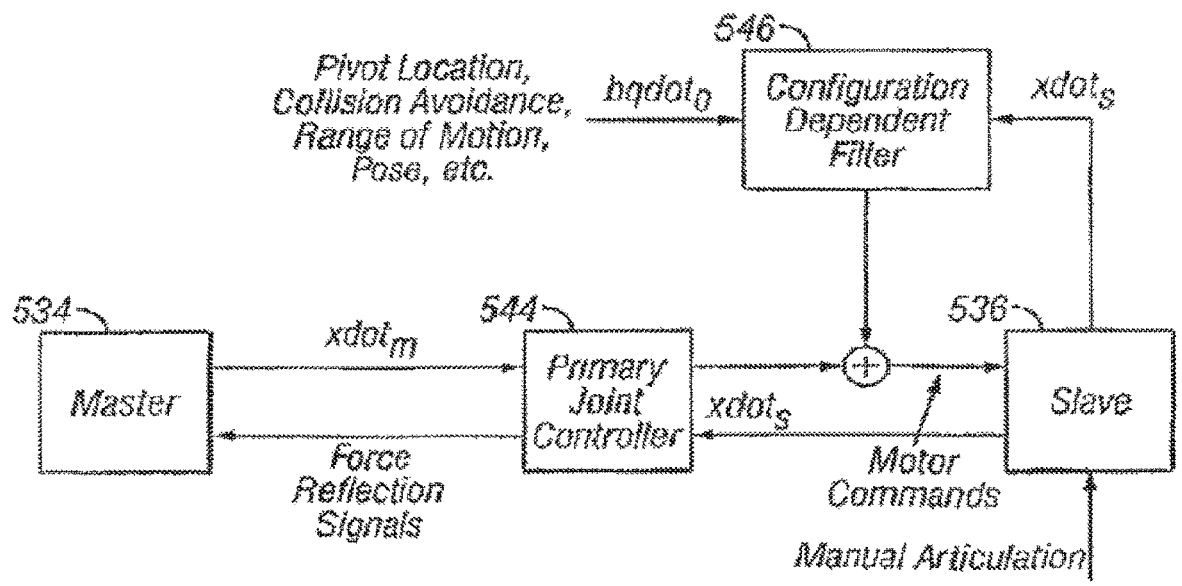
FIG. 18 illustrates a refinement of the simplified master-slave control illustrated in FIG. 17.

FIG. 18 illustrates a refinement of the simplified master-slave control schematic 540 from FIG. 17, and shows how different modules might be used in different processor modes. As illustrated in FIG. 18, first module 544 may, for example, comprise some form of a Jacobian controller having a Jacobian-related matrix. Second module 546 may, in a port clutch mode, receive signals from the slave manipulator 536 indicating a position or velocity of the slave generated at least in part by manual articulation of the slave manipulator linkage. In response to this input, the second module 546 can generate motor commands appropriate for driving the joints of the slave so as to allow the manual articulation of the slave linkage while configuring the slave in the desired joint configuration. During master-slave end effector manipulation, the controller may use second module 546 to help derive motor commands based on a different signal bqdot$_0$. This alternative input signal to the second module 546 of controller 542 may be used to drive the manipulator linkage so as to maintain or move the minimally invasive aperture pivot location along the manipulator structure, so as to avoid collisions between a plurality of manipulators, so as to enhance a range of motion of the manipulator structure and/or avoid singularities, so as to produce a desired pose of the manipulator, or the like. Hence, bqdot$_0$ can generally comprise and/or indicate (for example) a desired set of joint velocities, more generally representing a secondary control goal, typically in joint space. In other embodiments, the processor may include separate modules and/or dependent configuration filters for clutching, secondary controller tasks, and the like.

Figure 20:
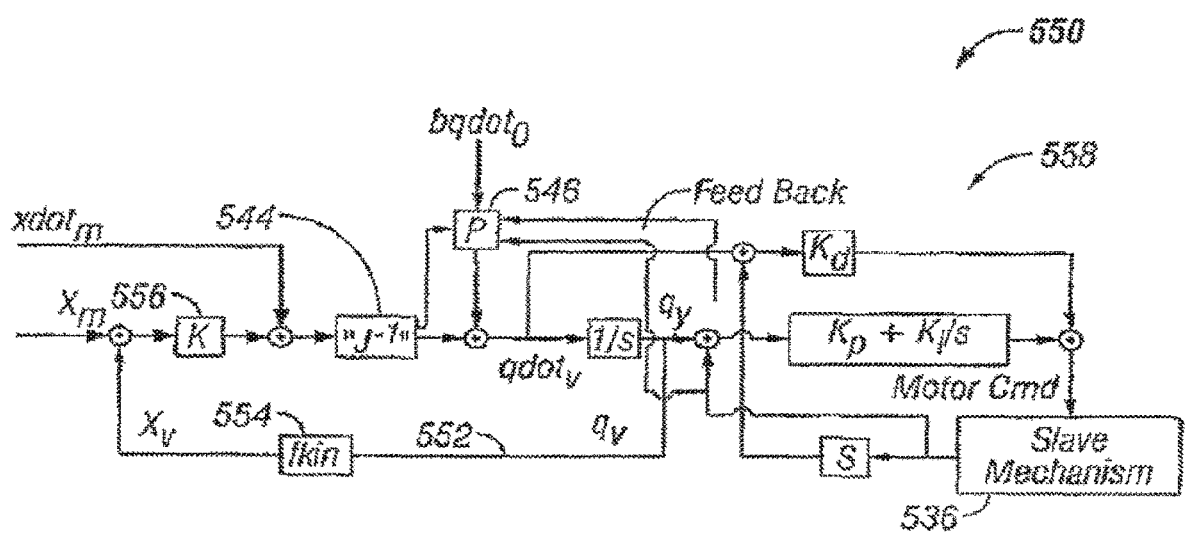
FIG. 20 schematically illustrates a modified portion of the controller of FIG. 11, in which the inverse Jacobian controller has been modified with a configuration dependent filter so that the controller respects priority of differing levels of system constraints and/or goals.
Figure 19:
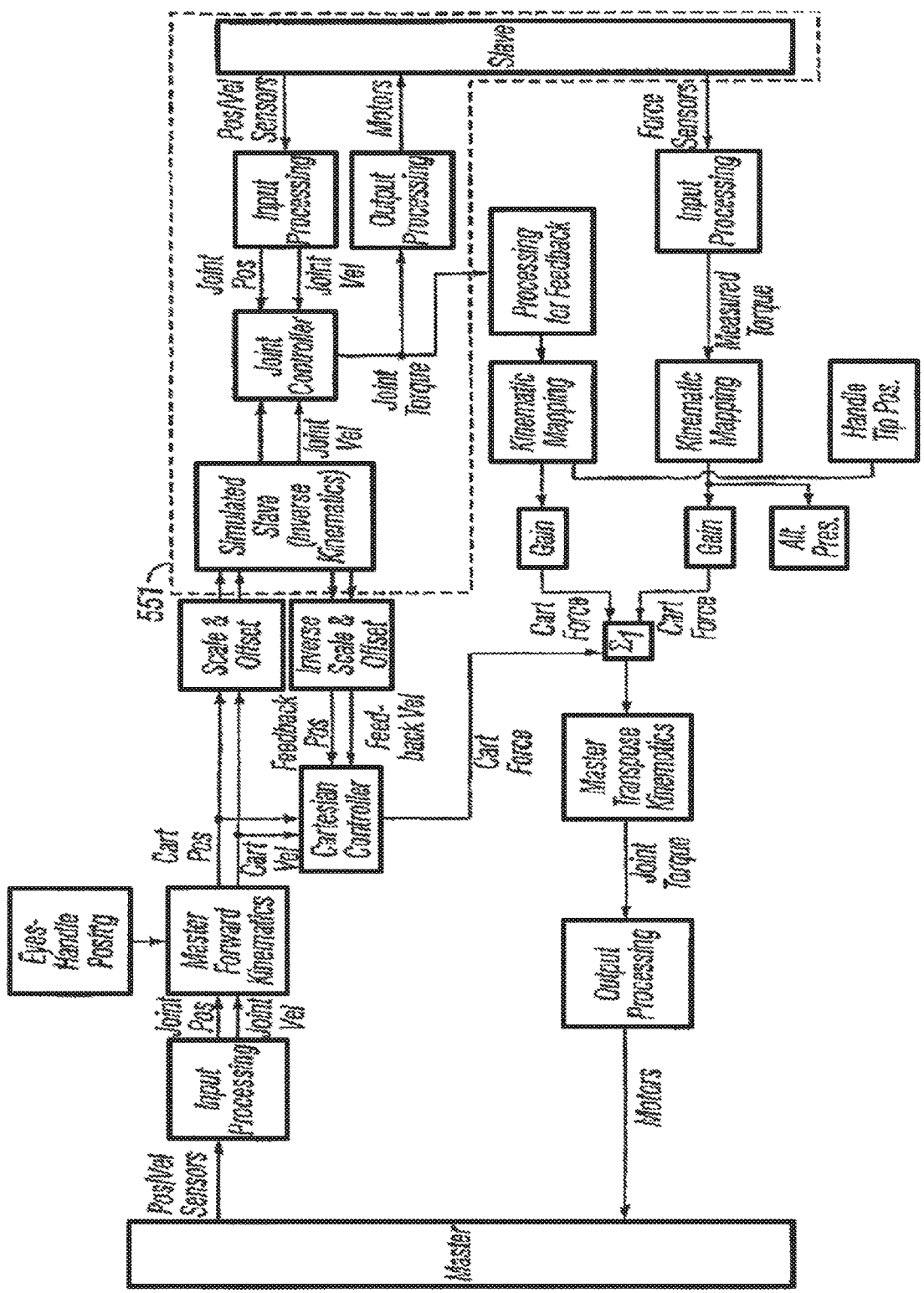
FIG. 19 schematically illustrates an exemplary inverse Jacobian controller for a fully constrained master/slave robotic surgical system.

Referring now to FIG. 20, a partial control schematic 550 illustrates modifications of the controller illustrated in FIG. 19. Control schematic 550 very roughly represents a modification of portion 551 of the controller of FIG. 11 to facilitate control over manipulator assemblies have large numbers of degrees of freedom. In the embodiment illustrated in FIG. 20, the first module 544 comprises an inverse Jacobian velocity controller, with the output from calculations made using an inverse Jacobian matrix modified according to a virtual slave path 552. First describing the virtual slave path, vectors associated with the virtual slave are generally indicated by a v subscript, so that a virtual slave velocity in joint space qdot$_v$ is integrated to provide q$_v$, which is processed using an inverse kinematic module 554 to generate a virtual slave joint position signal x$_v$. The virtual slave position and master input command x$_m$ are combined and processed using forward kinematics 556. The use of a virtual slave (often having simplified dynamics) facilitates smooth control and force reflection when approaching hard limits of the system, when transgressing soft limits of the system, and the like, as can be more fully understood with reference to the '885 patent previously incorporated herein by reference. Similarly, calculation of motor commands such as joint torque signals or the like from joint controllers in response to the output from the inverse Jacobian matrix (as modified or augmented by the second module 546) via appropriate joint controllers, input and output processing, and the like are more fully described in the '885 patent.

Addressing the structure generally indicated by the first and second control modules 544, 546, and of the other components of control schematic 550 and other controllers described herein, these structures will often comprise data processing hardware, software, and/or firmware. Such structures will often include reprogrammable software, data, and the like, which may be embodied in machine-readable code and stored in a tangible medium for use by processor 43 of surgeon console 40 (see FIG. 2). The machine-readable code may be stored in a wide variety of different configurations, including random access memory, non-volatile memory, write-once memory, magnetic recording media, optical recording media, and the like. Signals embodying the code and/or data associated therewith may be transmitted by a wide variety of communication links, including the Internet, an intranet, an Ethernet, wireless communication networks and links, electrical signals and conductors, optical fibers and networks, and the like. Processor 43 may, as illustrated in FIG. 2, comprise one or more data processors of surgeon console 40, and/or may include localized data processing circuits of one or more of the manipulators, the instruments, a separate and/or remote processing structure or location, and the like, and the modules described herein may comprise (for example) a single common processor board, a plurality of separate boards, or one or more of the modules may be separated onto a plurality of boards, some of which also run some or all of the calculation of another module. Similarly, the software code of the modules may be written as a single integrated software code, the modules may each be separated into individual subroutines, or parts of the code of one module may be combined with some or all of the code of another module. Hence, the data and processing structures may include any of a wide variety of centralized or distributed data processing and/or programming architectures.

Addressing the output of the controller of FIG. 20 in more detail, the controller will often seek to solve for one particular manipulator joint configuration vector q for use in generating commands for these highly configurable slave manipulator mechanisms. As noted above, the manipulator linkages often have sufficient degrees of freedom so as to occupy a range of joint states for a given end effector state. Such structures may (but will often not) comprise linkages having true redundant degrees of freedom, that is, structures in which actuation of one joint may be directly replaced by a similar actuation of a different joint along the kinematic chain. Nonetheless, these structures are sometimes referred to as having excess, extra, or redundant degrees of freedom, with these terms (in the broad sense) generally encompassing kinematic chains in which (for example) intermediate links can move without changing the position (including both location and orientation) of an end effector.

When directing movement of highly configurable manipulators using the velocity controller of FIG. 20, the primary joint controller of the first module often seeks to determine or solve for a virtual joint velocity vector qdot$_v$ that can be used to drive the joints of slave manipulator 536 in such a way that the end effector will accurately follow the master command x$_m$. However, for slave mechanisms with redundant degrees of freedom, an inverse Jacobian Matrix generally does not fully define a joint vector solution. For example, the mapping from Cartesian command xdot to joint motion qdot in a system that can occupy a range of joint states for a given end effector state is a mapping of one-to-many. In other words, because the mechanism is redundant, there are a mathematically infinite number of solutions, represented by a subspace in which the inverse lives. The controller may embody this relationship using a Jacobian matrix that has more columns than rows, mapping a plurality of joint velocities into comparatively few Cartesian velocities. Our solution $J^{-1}\dot{x}$ will often seek to undo this collapsing of the degrees of freedom of the slave mechanism into the Cartesian workspace.

Additional descriptions pertaining to using a processor configured by software instructions to calculate a software-constrained remote center of motion of the robotic manipulator arm assembly can be found in U.S. Pat. No. 8,004,229, which is hereby incorporated by reference in its entirety.

In short, the above descriptions (and the descriptions in U.S. Pat. No. 8,004,229) enable the pivot point (remote center of motion) to be determined/estimated through software, hence the notion of a software-constrained remote center of motion. By having the capability to compute software pivot points, different modes characterized by the compliance or stiffness of the system can be selectively implemented. More particularly, different system modes over a range of pivot points/centers (i.e., ranging from one have a passive pivot point to one having a fixed/rigid pivot point) can be implemented after an estimate pivot point is computed. For example, in a fixed pivot implementation, the estimated pivot point can be compared to a desired pivot point to generate an error output which can be used to drive the instrument's pivot to the desired location. Conversely, in a passive pivot implementation, while the a desired pivot location may not be an overriding objective, an estimated pivot point can be used for error detection and consequently safety because changes in estimated pivot point locations may indicate that the patient has been moved or a sensor is malfunctioning thereby giving the system an opportunity to take corrective action.

The interaction between the moving instrument and the tissue of the minimally invasive aperture may be determined at least in part by the processor, the processor optionally allowing the compliance or stiffness of the system to be changed throughout a range extending from a passive pivot point to a fixed pivot point. At the passive end of the passive/rigid range, the proximal end of the instrument may be moved in space while the motors of the instrument holder wrist joint apply little or no torque, so that the instrument acts effectively like it is coupled to the manipulator or robotic arm by a pair of passive joints. In this mode, the interaction between the instrument shaft and the tissue along the minimally invasive aperture induces the pivotal motion of the instrument about the pivot point. If the surgical instrument was not inserted into the minimally invasive aperture or otherwise constrained, it may point downward under the influence of gravity, and movement of the manipulator arm would translate the hanging instrument without pivotal motion about a site along the instrument shaft. Toward the rigid end of the passive/rigid range, the location of the minimally invasive aperture may be input or calculated as a fixed point in space. The motors associated with each joint of the kinematic chain disposed proximal of the pivot point may then drive the manipulator so that any lateral force laterally against the shaft at the calculate pivot point results in a reaction force to keep the shaft through the pivot point. Such a system may, in some ways, behave similar to mechanically constrained remote center linkages. Many embodiments will fall between these two extremes, providing calculated motion which generally pivots at the access site, and which adapts or moves the pivotal center of motion within an acceptable range when the tissue along the minimally invasive access site moves, without imposing excessive lateral forces on that tissue.

Figure 21:
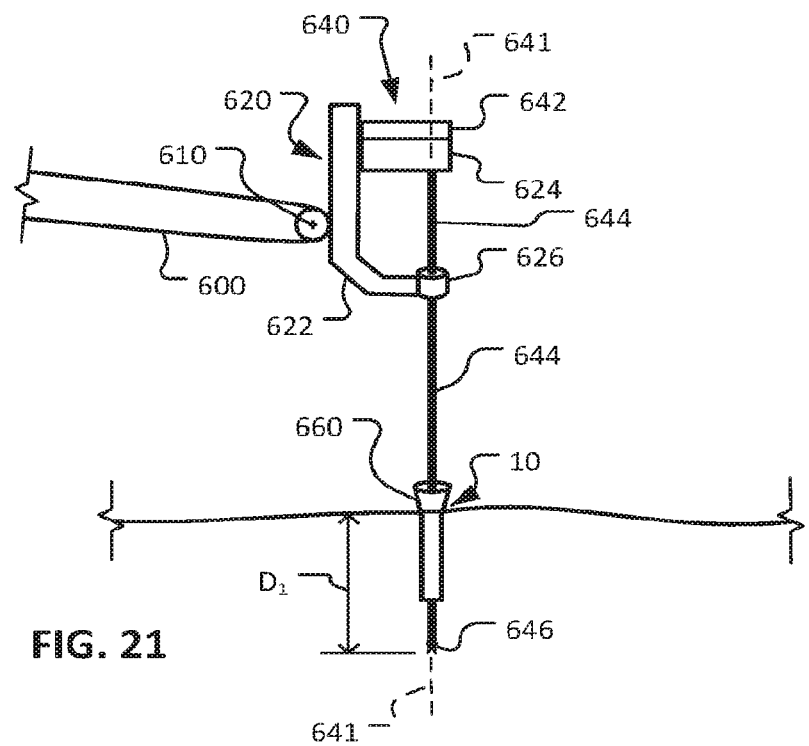
FIG. 21 is a side view of a distal portion of an example patient-side robotic manipulator assembly in accordance with some embodiments. The robotic manipulator assembly is in a first arrangement relative to a surgical site.
Figure 22:
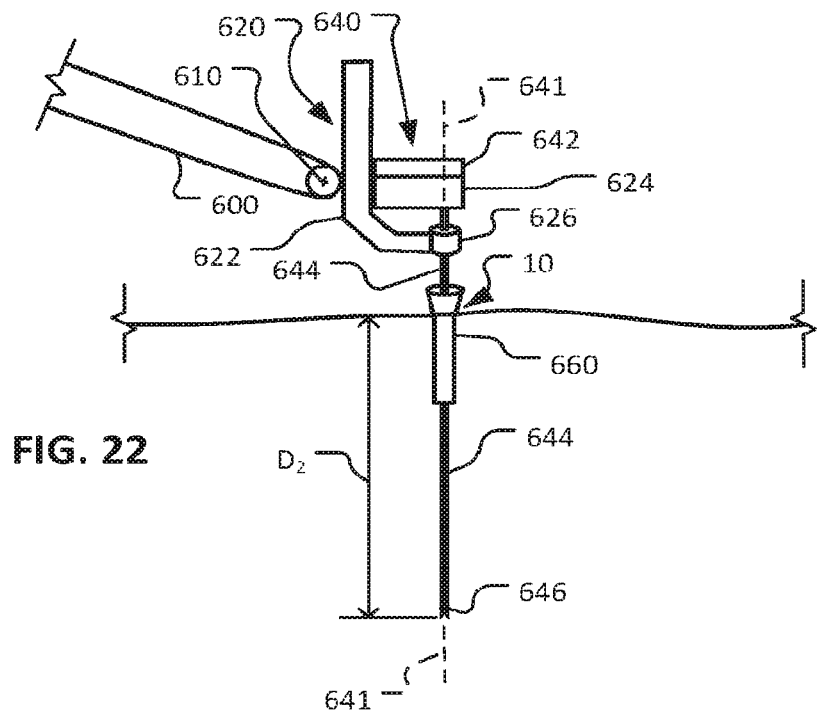
FIG. 22 is another side view of the example patient-side robotic manipulator assembly of FIG. 21. The robotic manipulator assembly is in a second arrangement relative to the surgical site.

Referring to FIGS. 21 and 22, an example instrument holder 620 is pivotably coupled at a joint 610 to a distal-most link 600 of a robotic manipulator arm assembly in a configuration that can be used to perform telesurgery in accordance with the telesurgical systems and concepts described herein. A surgical instrument 640 is releasably coupled to instrument holder 620. A cannula 660 is located at a minimally invasive surgical interface site 10. In the depicted embodiment, the cannula 660 is detached from the instrument holder 620. While in the depicted embodiment the instrument holder 620 is pivotably coupled to the distal-most link 600 of the robotic manipulator arm assembly, in some embodiments a translating coupling or a prismatic joint coupling is used to couple the instrument holder 620 to the distal-most link 600. Such pivoting, translating, and/or prismatic joints can be incorporated in any of the embodiments described herein.

The instrument holder 620 includes an instrument holder frame 622, and instrument holder carriage 624, and an optional instrument shaft guide 626. The instrument holder carriage 624 is movably coupled to the instrument holder frame 622. More particularly, the instrument holder carriage 624 is linearly translatable along the instrument holder frame 622. In some embodiments, the movement of the instrument holder carriage 624 along the instrument holder frame 622 is a motorized, translational movement that is actuatable/controllable by a processor of the telesurgical system. The optional instrument shaft guide 626 can be affixed to, or releasably coupleable to, the instrument holder frame 622.

The surgical instrument 640 includes a transmission assembly 642, an elongate shaft 644, and an end effector 646. The transmission assembly 642 is releasably coupleable with the instrument holder carriage 624. The shaft 644 extends distally from the transmission assembly 642. The shaft 644 is slidably coupled with a lumen defined by the cannula 660 and with a lumen defined by the optional instrument shaft guide 626. The end effector 646 is disposed at a distal end of the shaft 644, and is located within a surgical workspace within the body of the patient during the telesurgery procedure.

The elongate shaft 644 defines an instrument axis, this particular instrument axis being a longitudinal axis 641. By virtue of the physical engagement between the shaft 644 and the cannula 660, the longitudinal axis 641 is coincident with a longitudinal axis of the cannula 660. As the instrument holder carriage 624 translates along the instrument holder frame 622, the elongate shaft 644 of the surgical instrument 640 moves along the longitudinal axis 641. The longitudinal axis 641 remains fixed in space as the instrument holder carriage 624 translates along the instrument holder frame 622. In that manner (by translating the instrument holder carriage 624 along the instrument holder frame 622), the end effector 646 can be inserted into and/or retracted from the surgical workspace within the body of the patient along a line (defined by the longitudinal axis 641) that is fixed in space.

Additionally, in the depicted embodiment, the end effector 646 can be inserted into and/or retracted from the surgical workspace along the line fixed in space (defined by the longitudinal axis 641) in a second manner. That is, using the software-constrained remote center of motion techniques described herein, movement of the distal-most link 600 of the robotic manipulator arm assembly in combination with movement of the pivotable joint 610 can result in moving the surgical instrument 640 along the longitudinal axis 641 while the longitudinal axis 641 remains fixed in space.

In some embodiments, the cannula 660 is curved (in contrast to the linear cannula 660 shown) and the elongate shaft 644 of the surgical instrument 640 is flexible such that the elongate shaft 644 can conform to the curve of the cannula 660. In such a case, the end portion of the elongate shaft 644 that linearly extends from the transmission assembly 642 proximal to the curved cannula 660 defines the longitudinal axis 641. It should be understood that any of the embodiments described herein can alternatively include a curved cannula.

In some embodiments, the elongate shaft 644 of the surgical instrument 640 is curved (in contrast to the linear elongate shaft 644 shown). In such a case, the longitudinal axis 641 is a curved line that is coincident with the curved elongate shaft 644. It should be understood that any of the embodiments described herein can alternatively include a surgical instrument with a curved elongate shaft.

FIG. 21 shows the end effector 646 inserted at a first depth $D_1$. FIG. 22 shows the end effector 646 inserted at a second depth $D_2$. The second depth $D_2$ is greater than the first depth $D_1$. In both configurations, the longitudinal axis 641 is located along the same line in space.

Transforming from the arrangement of FIG. 21 to the arrangement of FIG. 22, can involve two types of movements. First, the instrument holder carriage 624 is translated along the instrument holder frame 622, resulting in a first movement of the surgical instrument 640 deeper into the patient. Second, movement of the distal-most link 600 of the robotic manipulator arm assembly in combination with movement of the pivotable joint 610 results in a second movement of the surgical instrument 640, still deeper into the patient. The difference between the second depth $D_2$ and the first depth $D_1$ is made up of the sum of the first and second movements. Both types of movements can be made while keeping the longitudinal axis 641 fixed (consistently coincident) along a line in space.

While the immediately preceding description involves two movements both of which result in moving the surgical instrument 640 deeper into the patient, it should be understood that the same principles are applicable for retracting the surgical instrument 640 from the patient. Moreover, any combination of the aforementioned first and second movements can be performed. For example, a first movement of the instrument holder carriage 624 along the instrument holder frame 622 can be made to retract the surgical instrument 640 from the patient, and a second movement of the robotic manipulator arm's distal-most link 600 and the pivotable joint 610 can be made to insert the surgical instrument 640 into the patient. Such movements can be made concurrently (contemporaneously) or sequentially (noncontemporaneously).

Figure 23:
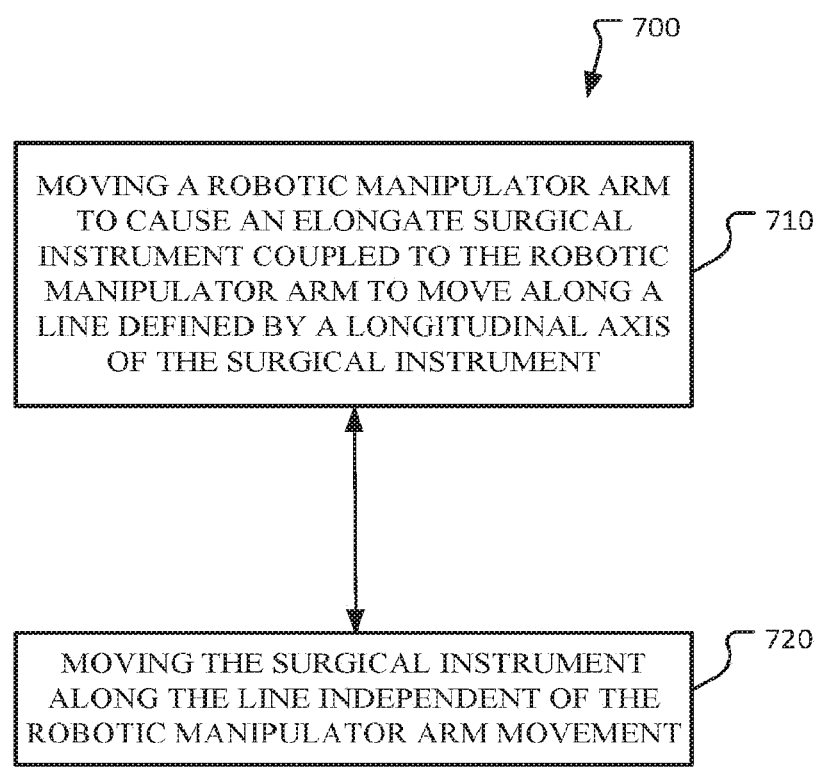
FIG. 23 is a flowchart of a two-stage method for controlling insertion of a surgical instrument in accordance with some embodiments.

Referring also to FIG. 23, a flowchart of a two-step method 700 for moving a surgical instrument along a line fixed in space is presented. The method 700 uses the concepts described above in reference to FIGS. 21 and 22.

In operation 710, a robotic manipulator arm is moved to cause an elongate surgical instrument coupled to the robotic manipulator arm to move along a fixed line in space that is defined by a longitudinal axis of the surgical instrument. Such a movement can be illustrated, for example, by a comparison between FIGS. 21 and 22. In FIG. 22, the distal-most link 600 of the robotic manipulator arm assembly is closer to the patient than in FIG. 21. As described above, as the distal-most link 600 was moved closer to the patient, the surgical instrument 640 was correspondingly moved along the longitudinal axis 641 that was consistently maintained along a line fixed in space. Said differently, using the software-constrained remote center of motion techniques described herein, movement of the distal-most link 600 of the robotic manipulator arm assembly can result in moving the surgical instrument 640 along the longitudinal axis 641 while the longitudinal axis 641 remains fixed in space. The movement of the distal-most link 600 may be made in coordination with movement of the pivotable joint 610. Alternatively, in some cases as the robotic manipulator arm is moved to cause the elongate surgical instrument to extend deeper into the surgical space, instrument may be experiencing pitch and yaw motions about the remote center while the instrument depth is also being controlled. Three-dimensional end-effector trajectories may be composed of some variations in pitch, yaw, and insertion of the instrument. In such a case, the longitudinal axis of the surgical instrument is not necessarily fixed in space.

In operation 720, the surgical instrument is moved along the fixed line in space (as defined by the longitudinal axis 641, per operation 710) independent of the robotic manipulator arm movement. For example, again referring to a comparison between FIGS. 21 and 22, the instrument holder carriage 624 can be translated along the instrument holder frame 622, resulting in a movement of the surgical instrument 640 along the longitudinal axis 641 while the longitudinal axis 641 remains fixed in space. Such a movement can be made independent of the movement of the distal-most link 600 of the robotic manipulator arm assembly.

In some cases, operation 720 may include periodically re-centering the instrument holder carriage 624 on the instrument holder frame 622. By re-centering the instrument holder carriage 624 on the instrument holder frame 622, approximately one-half of the full travel of the instrument holder carriage 624 relative to the instrument holder frame 622 is made available for movements in either direction (insertion and retraction). As the re-centering motion(s) is taking place, in some cases the position of the end effector 646 can be held substantially stationary.

In some cases, limitations can be established regarding the movements of the robotic manipulator arm and/or the instrument holder carriage (with respect to operations 710 and 720). In one such example, referring to the embodiment of FIGS. 21 and 22, in some cases the insertion of the instrument holder frame 622 is limited so that the instrument holder frame 622 will not collide with the cannula 660. In another example, in some cases the combined retraction of the instrument holder carriage 624 and the instrument holder frame 622 is limited so that the instrument end effector 646 does not get pulled out of the cannula 660. In another example, in some cases the distance that the instrument holder frame 622 is allowed to be retracted from the cannula 660 is limited, and any farther retractions along the longitudinal axis 641 are made by movements of the instrument holder carriage 624.

It should be understood that the operations 710 and 720 can be performed in either order without departing from the scope of the method 700. Moreover, the operations 710 and 720 can be performed concurrently (contemporaneously) or sequentially (noncontemporaneously) without departing from the scope of the method 700.

The use of method 700 can provide advantages pertaining to the design and operation of telesurgical systems. For example, because movements of the instrument holder carriage 624 along the instrument holder frame 622 involve relatively low inertia, operation 720 can be particularly well-suited to actuating short, quick movements of the surgical instrument 640, whereas longer, slower movements can be performed by moving the robotic manipulator arm as in operation 710. Having such a combination of movements available in accordance with method 700, the robotic manipulator arm and/or the instrument holder 620 can be made smaller and lighter. Therefore, the potential for interference between a system's robotic manipulator arm assemblies is lessened. In addition, the use of less powerful motors for actuation of the system's robotic manipulator arm assemblies and lighter weight links may be made feasible by the use of method 700.

In some embodiments, slow movements (i.e., those movements designated for performance by the robotic manipulator arm) can be differentiated from quick movements (i.e., those movements designated for performance by the instrument holder carriage) by defining a frequency cut off. For example, in some embodiments the controller uses a low-pass filtering operation on the desired motion of the instrument and uses the output of this filter to drive the motion of the robotic manipulator arm. The remaining high frequency motion components are used by the controller to drive the motion of the instrument holder carriage. Conversely, in some embodiments the control system filters the desired motion of the instrument using a high-pass filter and uses the output of this filter to drive the motion of the instrument holder carriage, while using the remaining portion of the signal to drive the motion of the robotic manipulator arm.

Figure 24:
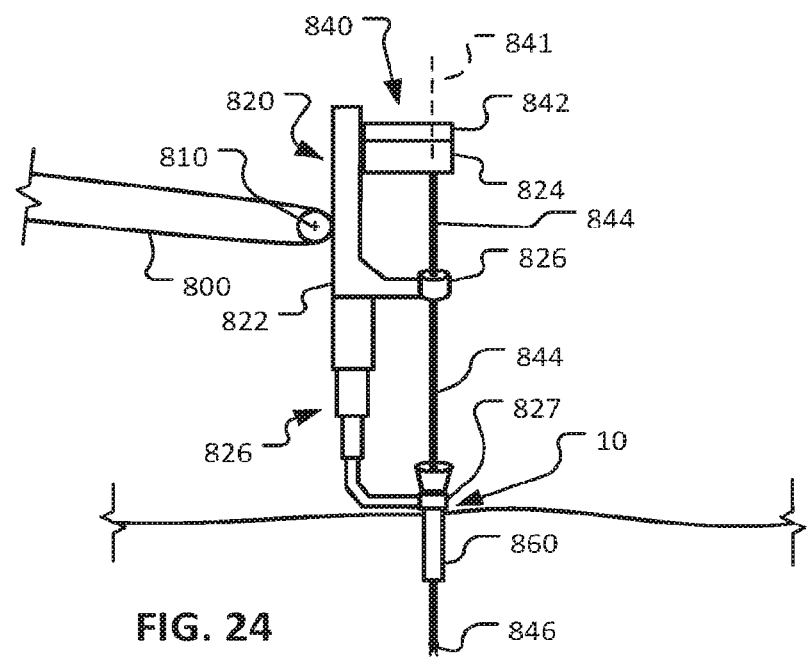
FIG. 24 is a side view of a distal portion of another example patient-side robotic manipulator assembly in accordance with some embodiments.

Referring to FIG. 24, an example instrument holder 820 is pivotably coupled at a joint 810 to a distal-most link 800 of a robotic manipulator arm assembly in a configuration that can be used to perform telesurgery in accordance with the telesurgical systems and concepts described herein. A surgical instrument 840 is releasably coupled to instrument holder 820. A cannula 860 is located at a minimally invasive surgical interface site 10.

The depicted arrangement is generally analogous to that of FIGS. 21 and 22, with the exception that, in the depicted arrangement, the cannula 860 is coupled to the instrument holder 820 via a linearly adjustable assembly 826 (whereas in FIGS. 21 and 22 the cannula 660 is detached from the instrument holder 620). The linearly adjustable assembly 826 extends from the instrument holder 820. A cannula clamp 827 can be located at the free end of the linearly adjustable assembly 826. The cannula clamp 827 can be used to releasably couple the cannula 860 to the instrument holder 820 via the linearly adjustable assembly 826. Such an arrangement can support lateral loads applied to the instrument shaft 844 and may help prevent the cannula 860 from shifting in relation to the surgical interface site 10.

In some embodiments, the linearly adjustable assembly 826 is active. That is, in some embodiments the linearly adjustable assembly 826 is driven by an actuator (e.g., a motor), such that the linearly adjustable assembly 826 extends and retracts by powered actuation. Such powered actuation can be actuated/controlled by a processor of a surgeon console (e.g., as per FIG. 2). In some embodiments, the linearly adjustable assembly 826 is passive. That is, in some embodiments the linearly adjustable assembly 826 is not driven by an actuator. Instead, the linearly adjustable assembly 826 may extend and retract in response to being acted on by external forces from contact with adjacent objects, gravity, and the like. In some passive and/or active embodiments, the linearly adjustable assembly 826 is braked so as to be able to hold its position when needed.

It should be recognized that the arrangement depicted in FIG. 24 can be operated in accordance with method 700 of FIG. 23. That is, using the software-constrained remote center of motion techniques described herein, the distal-most link 800 of the robotic manipulator arm assembly can be moved to result in moving the surgical instrument 840 along the longitudinal axis 841 while the longitudinal axis 841 remains fixed in space. In addition, the instrument holder carriage 824 can be translated along the instrument holder frame 822, resulting in a movement of the surgical instrument 840 along the longitudinal axis 841 while the longitudinal axis 841 remains fixed in space. Such a movement can be made independent of the movement of the distal-most link 800 of the robotic manipulator arm assembly.

Figure 25:
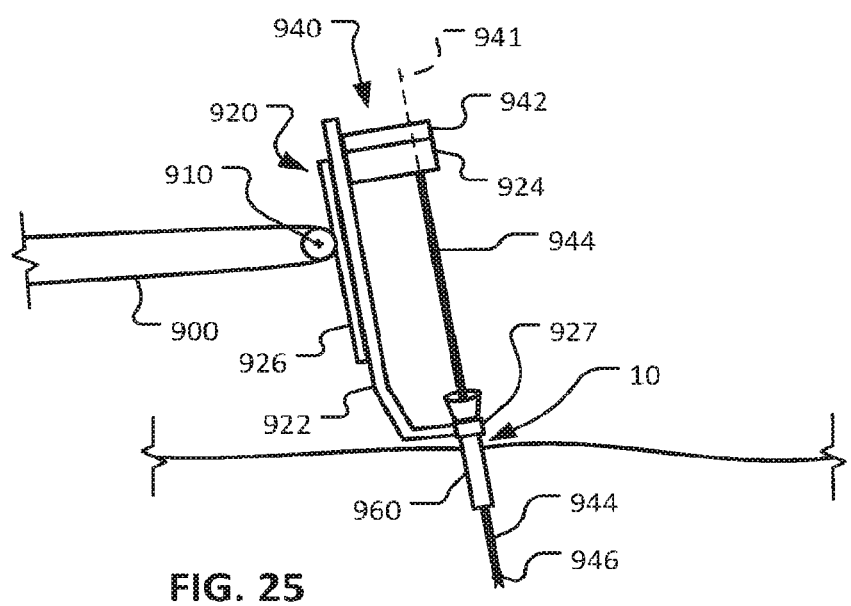
FIG. 25 is a side view of a distal portion of another example patient-side robotic manipulator assembly in accordance with some embodiments.

Referring to FIG. 25, an example instrument holder 920 is pivotably coupled at a joint 910 to a distal-most link 900 of a robotic manipulator arm assembly in a configuration that can be used to perform telesurgery in accordance with the telesurgical systems and concepts described herein. A surgical instrument 940 is releasably coupled to instrument holder 920. A cannula 960 is located at a minimally invasive surgical interface site 10.

The depicted arrangement includes a linear actuator mechanism 926 that facilitates translation of the joint 910 along the instrument holder frame 922. Therefore, the instrument holder 920 can pivot and translate in relation to the distal-most link 900. In some embodiments, the linear actuator mechanism 926 can be a mechanism such as, but not limited to, a lead screw assembly, a rack and pinion gear arrangement, a telescoping assembly, and the like.

It should be recognized that the arrangement depicted in FIG. 25 can be operated in accordance with method 700 of FIG. 23. That is, using the software-constrained remote center of motion techniques described herein, the distal-most link 900 of the robotic manipulator arm assembly can be moved to result in moving the surgical instrument 940 along the longitudinal axis 941 while the longitudinal axis 941 remains fixed in space. In addition, the instrument holder carriage 924 can be translated along the instrument holder frame 922, resulting in a movement of the surgical instrument 940 along the longitudinal axis 941 while the longitudinal axis 941 remains fixed in space. Such a movement can be made independent of the movement of the distal-most link 900 of the robotic manipulator arm assembly.

Figure 26:
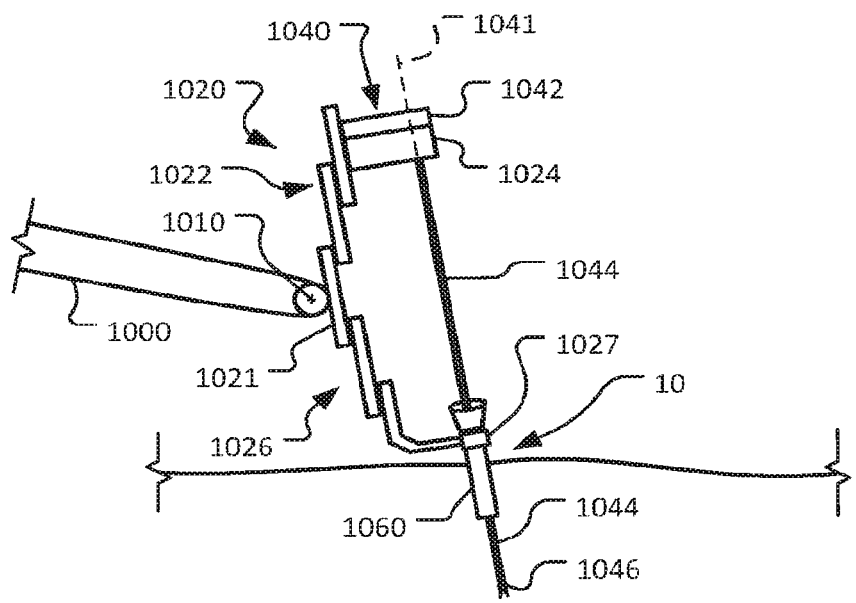
FIG. 26 is a side view of a distal portion of another example patient-side robotic manipulator assembly in accordance with some embodiments.

Referring to FIG. 26, an example instrument holder 1020 is pivotably coupled at a joint 1010 to a distal-most link 1000 of a robotic manipulator arm assembly in a configuration that can be used to perform telesurgery in accordance with the telesurgical systems and concepts described herein. A surgical instrument 1040 is releasably coupled to instrument holder 1020. A cannula 1060 is located at a minimally invasive surgical interface site 10.

The instrument holder 1020 includes a linearly adjustable upper portion 1022 and a linearly adjustable lower portion 1026. The linearly adjustable upper portion 1022 and the linearly adjustable lower portion 1026 are coupled to a middle portion 1021 that is pivotably coupled with the distal-most link 1000 at the joint 1010. The linearly adjustable portions 1022 and 1026 can be extended and/or retracted in relation to the middle portion 1021. In some embodiments, the linearly adjustable portions 1022 and 1026 are telescoping assemblies. In some embodiments, either of or both of the linearly adjustable portions 1022 and 1026 are active (power actuated). In some embodiments, either of or both of the linearly adjustable portions 1022 and 1026 are passive (not power actuated).

An instrument holder carriage 1024 is coupled with the linearly adjustable upper portion 1022. Hence, the instrument holder carriage 1024 can be translated (parallel to axis 1041) independent of the distal-most link 1000. The cannula 1060 is releasably coupleable to the linearly adjustable lower portion 1026 via a cannula clamp 1027. Hence, as the distal-most link 1000 moves, the cannula 1060 can be maintained in a generally stationary position in relation to the minimally invasive surgical interface site 10 (by compensatory movements of the linearly adjustable lower portion 1026).

It should be recognized that the arrangement depicted in FIG. 26 can be operated in accordance with method 700 of FIG. 23. That is, using the software-constrained remote center of motion techniques described herein, the distal-most link 1000 of the robotic manipulator arm assembly can be moved to result in moving the surgical instrument 1040 along the longitudinal axis 1041 while the longitudinal axis 1041 remains fixed in space. In addition, the instrument holder carriage 1024 can be translated along the instrument holder 1020 (in relation to middle portion 1021), resulting in a movement of the surgical instrument 1040 along the longitudinal axis 1041 while the longitudinal axis 1041 remains fixed in space. Such a movement can be made independent of the movement of the distal-most link 1000 of the robotic manipulator arm assembly.

Figure 27:
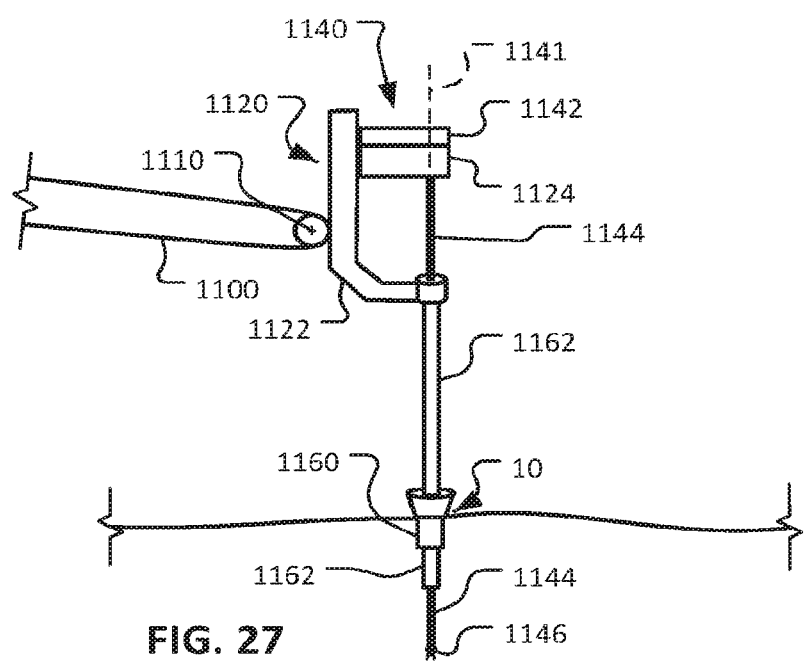
FIG. 27 is a side view of a distal portion of another example patient-side robotic manipulator assembly in accordance with some embodiments.

Referring to FIG. 27, an example instrument holder 1120 is pivotably coupled at a joint 1110 to a distal-most link 1100 of a robotic manipulator arm assembly in a configuration that can be used to perform telesurgery in accordance with the telesurgical systems and concepts described herein. A surgical instrument 1140 is releasably coupled to instrument holder 1120. A cannula 1160 is located at a minimally invasive surgical interface site 10.

The depicted arrangement is generally analogous to that of FIGS. 21 and 22, with the exception that, in the depicted arrangement, an inner cannula 1162 is coupled with the instrument holder 1120, and the inner cannula 1162 extends through the cannula 1160 located at the minimally invasive surgical interface site 10. The inner cannula 1162 is slidably coupled with a lumen defined by the cannula 1160. The elongate, instrument shaft 1144 of the surgical instrument 1140 is slidably coupled with a lumen defined by the inner cannula 1162. Such an arrangement can support lateral loads applied to the instrument shaft 1144 and may help prevent the cannula 1160 from shifting in relation to the surgical interface site 10. The inner cannula 1162 is longer than the cannula 1160.

It should be recognized that the arrangement depicted in FIG. 27 can be operated in accordance with method 700 of FIG. 23. That is, using the software-constrained remote center of motion techniques described herein, the distal-most link 1100 of the robotic manipulator arm assembly can be moved to result in moving the surgical instrument 1140 along the longitudinal axis 1141 while the longitudinal axis 1141 remains fixed in space. In addition, the instrument holder carriage 1124 can be translated along the instrument holder frame 1122, resulting in a movement of the surgical instrument 1140 along the longitudinal axis 1141 while the longitudinal axis 1141 remains fixed in space. Such a movement can be made independent of the movement of the distal-most link 1100 of the robotic manipulator arm assembly.

Figure 28:
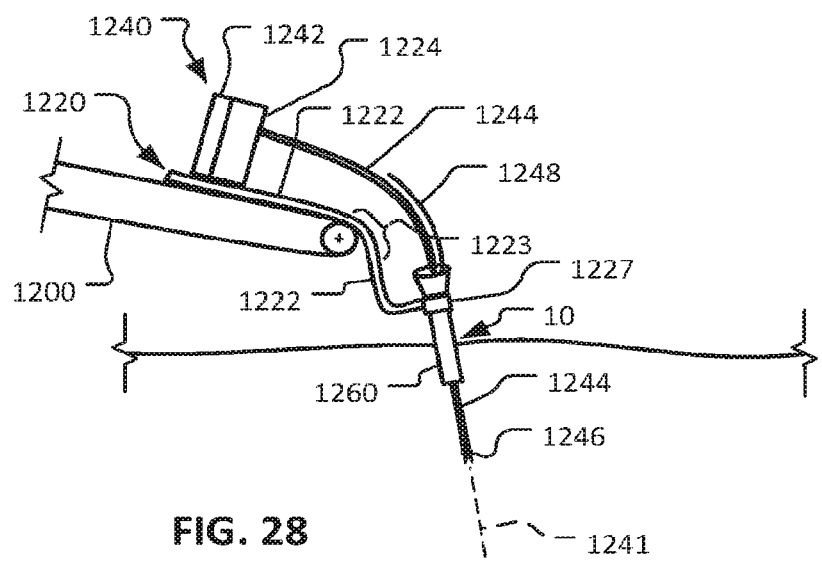
FIG. 28 is a side view of a distal portion of another example patient-side robotic manipulator assembly in accordance with some embodiments.

Referring to FIG. 28, an example instrument holder 1220 is coupled to a distal-most link 1200 of a robotic manipulator arm assembly in a configuration that can be used to perform telesurgery in accordance with the telesurgical systems and concepts described herein. A surgical instrument 1240 is releasably coupled to instrument holder 1220. A cannula 1260 is located at a minimally invasive surgical interface site 10.

The instrument holder 1220 includes an instrument holder frame 1222, an instrument holder carriage 1224, and a cannula clamp 1227. The instrument holder carriage 1224 is movably coupled to the instrument holder frame 1222. More particularly, the instrument holder carriage 1224 is linearly translatable along the instrument holder frame 1222. In some embodiments, the movement of the instrument holder carriage 1224 along the instrument holder frame 1222 is a motorized, translational movement that is actuatable/controllable by a processor of the telesurgical system. The cannula clamp 1227 can be affixed to the instrument holder frame 1222. The cannula clamp 1227 can adapt the instrument holder frame 1222 to releasably couple with the cannula 1260.

A proximal end portion of the instrument holder 1220 is coupled to the distal-most link 1200. The instrument holder 1220 includes an articulable portion of the instrument holder frame 1223. The articulable portion of the instrument holder frame 1223 can be manipulated in relation to the distal-most link 1200. In some embodiments, the articulable portion of the instrument holder frame 1223 can be manipulated by a motorized movement that is actuatable/controllable by a processor of the telesurgical system. By manipulating the instrument holder frame 1223 in relation to the distal-most link 1200, the orientation of the cannula 1260 can be adjusted. By adjusting the orientation of the cannula 1260, a distal portion of the surgical instrument 1240 can be physically controlled.

The surgical instrument 1240 includes a transmission assembly 1242, a flexible elongate shaft 1244, and an end effector 1246. The transmission assembly 1242 is releasably coupleable with the instrument holder carriage 1224. The flexible elongate shaft 1244 extends distally from the transmission assembly 1242. The flexible elongate shaft 1244 is slidably coupled with a lumen defined by the cannula 1260. In some embodiments, a guide member 1248 is included to facilitate the lateral flexure of the flexible elongate shaft 1244 between the transmission assembly 1242 and the cannula 1260. The end effector 1246 is disposed at a distal end of the flexible elongate shaft 1244, and is located within a surgical workspace within the body of the patient during the telesurgery procedure.

The cannula 1260 and the portion of the flexible elongate shaft 1244 that extends distally of the cannula 1260 define a longitudinal axis 1241. As the instrument holder carriage 1224 translates along the instrument holder frame 1222, the portion of the flexible elongate shaft 1244 that extends distally of the cannula 1260 moves along the longitudinal axis 1241. The longitudinal axis 1241 remains fixed in space as the instrument holder carriage 1224 translates along the instrument holder frame 1222. In that manner (by translating the instrument holder carriage 1224 along the instrument holder frame 1222), the end effector 1246 can be inserted into and/or retracted from the surgical workspace within the body of the patient along a line (defined by the longitudinal axis 1241) that is fixed in space.

Additionally, in the depicted embodiment, the end effector 1246 can be inserted into and/or retracted from the surgical workspace along the line fixed in space (defined by the longitudinal axis 1241) in a second manner. That is, using the software-constrained remote center of motion techniques described herein, movement of the distal-most link 1200 of the robotic manipulator arm assembly in combination with movement of the articulable portion of the instrument holder frame 1223 can result in moving the surgical instrument 1240 along the longitudinal axis 1241 while the longitudinal axis 1241 remains fixed in space.

It should be recognized that the arrangement depicted in FIG. 28 can be operated in accordance with method 700 of FIG. 23. That is, using the software-constrained remote center of motion techniques described herein, the distal-most link 1200 of the robotic manipulator arm assembly can be moved to result in moving the surgical instrument 1240 along the longitudinal axis 1241 while the longitudinal axis 1241 remains fixed in space. In addition, the instrument holder carriage 1224 can be translated along the instrument holder frame 1222, resulting in a movement of the surgical instrument 1240 along the longitudinal axis 1241 while the longitudinal axis 1241 remains fixed in space. Such a movement can be made independent of the movement of the distal-most link 1200 of the robotic manipulator arm assembly.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-assisted medical system comprising:
a manipulator arm; and
an instrument holder physically coupled to the manipulator arm by a joint at a distal-most link of the manipulator arm, the instrument holder configured to releasably couple to an instrument, wherein the instrument holder comprises:
an adjustable assembly, and
a cannula clamp physically coupled to the adjustable assembly, wherein a retraction or extension of the adjustable assembly moves the cannula clamp relative to the joint at the distal-most link of the manipulator arm, and wherein the cannula clamp is configured to releasably couple to a cannula configured to receive the instrument.

2. The computer-assisted medical system of claim 1, wherein the adjustable assembly comprises a telescoping assembly.

3. The computer-assisted medical system of claim 1, wherein the adjustable assembly comprises a linearly adjustable assembly.

4. The computer-assisted medical system of claim 1, further comprising:
a brake configured to hold a position of the adjustable assembly.

5. The computer-assisted medical system of claim 1, wherein the instrument holder further comprises:
an instrument holder frame;
an instrument holder carriage coupled to the instrument holder frame, the instrument holder carriage configured to releasably couple to the instrument, and the instrument holder carriage translatable along the instrument holder frame to move the instrument relative to the instrument holder frame.

6. The computer-assisted medical system of claim 5, further comprising:

a processor configured to cause the instrument holder carriage to periodically re-center relative to the instrument holder frame.

7. The computer-assisted medical system of claim 6, wherein the processor is configured to cause the instrument holder carriage to periodically re-center relative to the instrument holder frame by:
causing movement of the instrument holder carriage relative to the instrument holder frame while holding a position of an end effector of the instrument substantially stationary.

8. The computer-assisted medical system of claim 1, wherein the adjustable assembly further comprises: an intermediate component configured to receive a shaft of the instrument when the instrument is coupled to the instrument holder.

9. The computer-assisted medical system of claim 1, wherein the adjustable assembly comprises a lower adjustable assembly, and wherein the instrument holder further comprises: a rigid upper portion configured to couple to the instrument.

10. The computer-assisted medical system of claim 1, wherein the adjustable assembly comprises:
a first adjustable portion coupled to the cannula clamp; and
a second adjustable portion configured to physically couple to the instrument, wherein adjustment of the second adjustable portion moves the instrument relative to the manipulator arm when the instrument is coupled to the second adjustable portion.

11. The computer-assisted medical system of claim 10, wherein:
the first adjustable portion comprises a linearly adjustable lower linear portion;
the second adjustable portion comprises a linearly adjustable upper linear portion; and
the instrument holder further comprises a middle portion physically coupled to the first and second adjustable portions, the middle portion pivotably coupled to the manipulator arm.

12. The computer-assisted medical system of claim 1, wherein the adjustable assembly is passively adjustable to produce the physical adjustment retraction or extension.

13. The computer-assisted medical system of claim 1, further comprising:
an actuator configured to drive the retraction or extension of the adjustable assembly; and
a processor configured to control the actuator to drive the retraction or extension.

14. The computer-assisted medical system of claim 1, further comprising a processor, the processor configured to:
obtain a desired motion of the instrument, the desired motion including a longitudinal movement along a longitudinal axis of the instrument;
determine first and second motion components of the longitudinal movement, the first motion component for the manipulator arm, and the second motion for an instrument holder carriage of the instrument holder; and
cause the instrument to move in accordance with the longitudinal movement by:
causing motion the manipulator arm based on the first motion component, and
causing, based on the second motion component, motion of an instrument holder carriage relative to the manipulator arm, the instrument holder comprising the instrument holder carriage.

15. The computer-assisted medical system of claim 14, wherein when the longitudinal movement is a retraction movement, the processor is configured to determine the first and second motion components by: limiting a retraction of the instrument holder carriage.

16. The computer-assisted medical system of claim 1, wherein the instrument holder further comprises a moveable instrument holder carriage, and wherein the computer-assisted medical system further comprises:
actuators to move the manipulator arm and the instrument holder carriage; and
a processor configured to cause the actuators to move the manipulator arm and the instrument holder carriage while limiting at least one movement selected from the group consisting of: a movement of the manipulator arm and a movement of the instrument holder carriage.

17. The computer-assisted medical system of claim 16, wherein limiting the movement of the manipulator arm or the instrument holder carriage comprises:
limiting an insertion of the instrument holder carriage such that the instrument holder carriage does not collide with the cannula; or
limiting a retraction of the instrument holder carriage such that an end effector of the instrument is not pulled out of the cannula.

18. A method of operating a computer-assisted medical system comprising a manipulator arm and an instrument holder physically coupled to the manipulator arm by a joint at a distal-most link of the manipulator arm, the instrument holder configured to releasably couple to an instrument, the method comprising:
determining a retraction or extension of an adjustable assembly of the instrument holder, wherein the retraction or extension moves a cannula clamp physically coupled to the adjustable assembly relative to the joint at the distal-most link of the manipulator arm; and
driving an actuator to produce the retraction or extension.

19. The method of claim 18, wherein the instrument holder comprises an instrument holder frame and an instrument holder carriage configured to releasably couple to the instrument, the instrument holder carriage translatable along the instrument holder frame, and wherein the method further comprises:
commanding a periodic re-centering of the instrument holder carriage relative to the instrument holder frame.

20. The method of claim 19, wherein commanding the periodic re-centering comprises:
commanding a movement of the instrument holder carriage relative to the instrument holder frame while holding a position of an end effector of the instrument substantially stationary.

21. The method of claim 18, wherein the instrument holder comprises an instrument holder frame and an instrument holder carriage configured to releasably couple to the instrument, the instrument holder carriage translatable along the instrument holder frame, and wherein the method further comprises:
obtaining a desired motion of the instrument, the desired motion including a longitudinal movement along a longitudinal axis of the instrument;
determining first and second motion components of the longitudinal movement, the first motion component for the manipulator arm, and the second motion for the instrument holder carriage; and
causing the instrument to move in accordance with the longitudinal movement by:
causing motion of the manipulator arm based on the first motion component, and
causing motion of the instrument holder carriage relative to the instrument holder frame, based on the second motion component.

22. The method of claim 18, wherein the instrument holder comprises an instrument holder frame and an instrument holder carriage configured to releasably couple to the instrument, the instrument holder carriage translatable along the instrument holder frame, and wherein the method further comprises:
limiting at least one movement selected from the group consisting of: a movement of the manipulator arm and a movement of the instrument holder carriage.

23. A non-transitory computer readable medium configured for storing instructions executed by one or more processors of a medical system comprising a manipulator arm and an instrument holder physically coupled to the manipulator arm by a joint at a distal-most link of the manipulator arm, the instrument holder configured to releasably couple to an instrument, the medium comprising instructions causing the one or more processors to perform operations comprising:
determining a retraction or extension of an adjustable assembly of the instrument holder, wherein the retraction or extension moves a cannula clamp physically coupled to the adjustable assembly relative to the joint at the distal-most link of the manipulator arm; and
driving an actuator to drive the retraction or extension.

24. The non-transitory computer readable medium of claim 23, wherein the instrument holder comprises an instrument holder frame and an instrument holder carriage configured to releasably couple to the instrument, the instrument holder carriage translatable along the instrument holder frame, and wherein the operations further comprise:
commanding a periodic re-centering relative to the instrument holder frame; or
limiting at least one movement selected from the group consisting of: a movement of the manipulator arm and a movement of the instrument holder carriage.

* * * * *